US008200335B2

(12) United States Patent
Donofrio et al.

(10) Patent No.: US 8,200,335 B2
(45) Date of Patent: Jun. 12, 2012

(54) IMPLANTABLE MEDICAL DEVICE LEAD CONNECTION ASSEMBLY

(75) Inventors: William T. Donofrio, Andover, MN (US); John E. Burnes, Coon Rapids, MN (US); Paul G. Krause, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 618 days.

(21) Appl. No.: 12/363,375

(22) Filed: Jan. 30, 2009

(65) Prior Publication Data

US 2010/0114210 A1 May 6, 2010

Related U.S. Application Data

(60) Provisional application No. 61/110,241, filed on Oct. 31, 2008.

(51) Int. Cl.
*A61N 1/08* (2006.01)
*H01R 13/64* (2006.01)
(52) U.S. Cl. .......................................... 607/37; 439/909
(58) Field of Classification Search .............. 607/36–38; 439/909, 38–40, 129
See application file for complete search history.

(56) References Cited

U.S. PATENT DOCUMENTS

| 5,261,395 | A | | 11/1993 | Oleen et al. |
|---|---|---|---|---|
| 5,330,507 | A | * | 7/1994 | Schwartz ........................ 607/14 |
| 5,374,279 | A | | 12/1994 | Duffin, Jr. et al. |
| 5,388,578 | A | * | 2/1995 | Yomtov et al. ................ 600/375 |
| 5,522,856 | A | * | 6/1996 | Reineman ......................... 607/9 |
| 5,775,935 | A | * | 7/1998 | Barna ............................ 439/488 |
| 6,006,135 | A | | 12/1999 | Kast et al. |
| 6,134,470 | A | | 10/2000 | Hartlaub |
| 6,327,502 | B1 | | 12/2001 | Johansson et al. |
| 6,428,368 | B1 | | 8/2002 | Hawkins et al. |
| 6,847,845 | B2 | * | 1/2005 | Belden ........................... 607/37 |
| 7,096,064 | B2 | | 8/2006 | Deno et al. |
| 7,515,964 | B1 | * | 4/2009 | Alexander et al. .............. 607/38 |
| 7,567,841 | B2 | | 7/2009 | Chan |
| 2003/0073348 | A1 | | 4/2003 | Ries et al. |
| 2004/0034392 | A1 | | 2/2004 | Spadgenske |
| 2004/0116976 | A1 | | 6/2004 | Spadgenske |
| 2004/0193228 | A1 | | 9/2004 | Gerber |
| 2005/0065570 | A1 | | 3/2005 | Stein et al. |
| 2005/0070968 | A1 | | 3/2005 | Bergelson et al. |

(Continued)

OTHER PUBLICATIONS

International Preliminary Report on Patentability from international application No. PCT/US2009/062857, date May 12, 2011, 9 pp.

(Continued)

*Primary Examiner* — Carl H Layno
*Assistant Examiner* — Jessica Sarcione
(74) *Attorney, Agent, or Firm* — Carol F. Barry

(57) ABSTRACT

A lead connection assembly of an implantable medical device (IMD) may include at least two different types of electrical connectors. In some examples, the lead connection assembly may include first and second electrical connectors that have at least one of a different electrical contact arrangement, a different lead connection receptacle geometry or a different size than the first electrical connector. The first electrical connector may be electrically connected to a first therapy module that generates cardiac rhythm therapy that is delivered to a heart of a patient, and the second electrical connector may be electrically connected to a second therapy module that generates electrical stimulation that is delivered to a tissue site within the patient. The second electrical connector may be configured to be incompatible with a lead that delivers the cardiac rhythm therapy to the patient.

31 Claims, 10 Drawing Sheets

U.S. PATENT DOCUMENTS

| | | | |
|---|---|---|---|
| 2005/0192639 A1 | 9/2005 | Bardy et al. | |
| 2005/0255719 A1* | 11/2005 | Heidlein | 439/39 |
| 2006/0004420 A1* | 1/2006 | Rossing et al. | 607/37 |
| 2006/0079942 A1 | 4/2006 | Deno et al. | |
| 2006/0217771 A1 | 9/2006 | Soykan et al. | |
| 2007/0123947 A1 | 5/2007 | Wenger et al. | |
| 2007/0255323 A1 | 11/2007 | Werder et al. | |
| 2007/0255331 A1 | 11/2007 | Gillberg et al. | |
| 2007/0276443 A1 | 11/2007 | Shafer et al. | |
| 2008/0015659 A1 | 1/2008 | Zhang et al. | |
| 2008/0208290 A1 | 8/2008 | Phillips et al. | |
| 2008/0242976 A1 | 10/2008 | Robertson et al. | |
| 2009/0112282 A1 | 4/2009 | Kast et al. | |
| 2010/0137929 A1* | 6/2010 | Libbey et al. | 607/5 |

OTHER PUBLICATIONS

U.S. Appl. No. 61/110,241, filed Oct. 31, 2008, entitled "Implantable Medical Device Lead Connection Assembly", by Donofrio et al.

U.S. Appl. No. 12/610,157, filed Oct. 30, 2009, entitled "Implantable Medical Device Including a Plurality of Lead Connection Assemblies", by Libbey et al.

International Search Report and Written Opinion from corresponding PCT/US2009/062857 mailed on Mar. 4, 2010 (15 pgs.).

Response to Office Action dated Sep. 2, 2011, from U.S. Appl. No. 12/610,157, filed Jan. 3, 2012, 15 pp.

Office Action from U.S. Appl. No. 12/610,157, dated Sep. 2, 2011, 9 pp.

* cited by examiner

IMPLANTABLE MEDICAL DEVICE LEAD CONNECTION ASSEMBLY

This application claims the benefit of U.S. Provisional Application No. 61/110,241, entitled, "IMPLANTABLE MEDICAL DEVICE LEAD CONNECTION ASSEMBLY," and filed on Oct. 31, 2008, the entire content of which is incorporated herein by reference.

TECHNICAL FIELD

The disclosure relates to medical devices and, in particular, implantable medical devices configured to deliver electrical stimulation to a patient.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an IMD housing as an alternative or in addition to electrodes or sensors deployed on one or more leads.

For example, implantable cardiac devices, such as cardiac pacemakers or implantable cardioverter defibrillators, provide therapeutic electrical stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation therapy to a patient's heart upon detecting ventricular fibrillation. Some medical device systems that include a neurostimulator in addition to implantable cardiac device have also been proposed.

SUMMARY

In general, the disclosure is directed to lead connection assemblies for implantable medical devices (IMDs). In some examples, a lead connection assembly of an IMD may include at least two different types of electrical connectors that are configured to electrically connect a respective implantable medical lead to one or more therapy modules of the IMD. In some examples, the IMD may include a lead connection assembly including a first electrical connector and a second electrical connector that has at least one of a different electrical contact arrangement, a different lead connection receptacle geometry or a different size than the first electrical connector. In this way, the electrical connectors may be configured to receive different types of leads.

In some examples, the IMD may include a first therapy module that is configured to deliver an electrical stimulation signal to a patient with one or more electrodes of a first lead that is electrically coupled to the first therapy module via the first electrical connector, and a second therapy module that is configured to deliver a second electrical stimulation signal to the patient with one or more electrodes of a second lead that is electrically coupled to the second therapy module via the second electrical connector. The second electrical connector may be incompatible with the first lead, e.g., to help prevent the first lead from being electrically connected to the second therapy module via the second electrical connector. In addition, in some examples, the first electrical connector may be incompatible with the second lead.

In some examples, the first therapy module may be configured to deliver at least one of pacing, cardioversion, or defibrillation therapy to the heart of a patient via the first lead, and the second therapy module may be configured to deliver an electrical stimulation signal to a nonmyocardial tissue site (e.g., a tissue site proximate a nerve and/or an extravascular tissue site) or a nonvascular cardiac tissue site (e.g., a cardiac fat pad) within the patient via the second lead. The mutually incompatible configurations of the second electrical connector and first lead may help prevent the first lead from delivering electrical stimulation generated by the second therapy module to the heart of a patient.

In some examples, a lead connection assembly of an IMD may include two or more electrical connectors that define openings for receiving leads, whereby the openings face in different directions. For example, a lead connection assembly may include a first electrical connector that receives a first lead such that the first lead extends from the housing of the IMD in a first direction, and a second electrical connector that receives a second lead such that the second lead extends from the housing in a second direction that is different than the first direction. In some example, the first and second directions may correspond to the different target tissue sites for delivery of the stimulation therapy by the first and second leads, respectively.

In one example, the disclosure is directed to an implantable medical system comprising a housing, a first therapy module enclosed within the housing and configured to generate at least one of a pacing, cardioversion or defibrillation therapy that is delivered to a heart of a patient, a second therapy module enclosed within the housing and configured to generate electrical stimulation that is delivered to a tissue site within the patient, and a lead connection assembly. The lead connection assembly comprises a first electrical connector electrically coupled to the first therapy module and configured to electrically connect to a first lead that delivers the at least one of the pacing, cardioversion or defibrillation therapy to the heart of the patient and a second electrical connector electrically coupled to the second therapy module and configured to electrically connect to a second lead that delivers the electrical stimulation to the tissue site. The second electrical connector is configured to be at least partially incompatible with the first lead.

In another example, the disclosure is directed to an implantable medical system comprising a housing, means for generating at least one of a pacing, cardioversion, or defibrillation therapy that is delivered to a heart of a patient, wherein the means for generating the at least one of pacing, cardioversion or defibrillation therapy is enclosed within the housing, means for generating electrical stimulation that is delivered to a tissue site within the patient, wherein the means for generating electrical stimulation is enclosed within the housing, and means for receiving leads. The means for receiving leads comprises means for electrically coupling a first lead to the means for generating the at least one of pacing, cardioversion or defibrillation therapy and means for electrically coupling a second lead to the means for generating the electrical stimulation. The means for electrically coupling the second lead to the means for generating electrical stimulation is configured to be at least partially incompatible with the first lead.

In another example, the disclosure is directed to a method comprising delivering at least one of pacing, cardioversion or defibrillation therapy to a heart of a patient with at least one electrode of a first lead that is electrically coupled to a first therapy module of an implantable medical device, wherein the implantable medical device comprises a first electrical connector that electrically connects the first lead to the first therapy module, and delivering electrical stimulation to a tissue site within the patient with at least one electrode of a second lead that is electrically coupled to a second therapy module of the implantable medical device, wherein the implantable medical device comprises a second electrical connector that electrically connects the second lead to the second therapy module, and wherein the second electrical connector is configured to be at least partially incompatible with the first lead.

In another example, the disclosure is directed to an implantable medical system comprising a housing a first therapy module enclosed within the housing and configured to generate at least one of a pacing, cardioversion or defibrillation therapy that is delivered to a heart of a patient, a second therapy module enclosed within the device housing and configured to generate electrical stimulation that is delivered to a tissue site within the patient, and a lead connection assembly. The lead connection assembly comprises a first electrical connector electrically coupled to the first therapy module and defining a first opening configured to receive a first lead that delivers the at least one of pacing, cardioversion or defibrillation therapy to the heart of the patient, and a second electrical connector electrically coupled to the second therapy module and defining a second opening configured to receive a second lead that delivers the electrical stimulation to the tissue site of the patient, where the first and second openings face different directions.

In another example, the disclosure is directed to a method comprising delivering at least one of pacing, cardioversion or defibrillation therapy to a heart of a patient via a first lead electrically coupled to a first therapy module of an implantable medical device via a first electrical connector of a lead connection assembly, and delivering electrical stimulation to a tissue site within the patient via a second lead electrically coupled to a second therapy module of the implantable medical device via a second electrical connector of the lead connection assembly. The first lead extends from a housing of the implantable medical device in a first direction and the second lead extends from the housing of the implantable medical device in a second direction that is different from the first direction.

In another example, the disclosure is directed to an implantable medical system comprising a housing; means for delivering at least one of a pacing, cardioversion, or defibrillation therapy to a heart of a patient, the means for delivering the at least one of pacing, cardioversion or defibrillation therapy to the heart of the patient enclosed within the housing; means for delivering electrical stimulation to a tissue site within the patient, the means for delivering electrical stimulation to the tissue site enclosed within the housing; and a lead connection assembly. The lead connection assembly comprising means for electrically coupling a first lead that delivers the at least one of pacing, cardioversion or defibrillation therapy to the means for delivering the at least one of pacing, cardioversion or defibrillation therapy, wherein the means for electrically coupling the first lead defines a first opening to receive the first lead; and means for electrically coupling a second lead that delivers the electrical stimulation to the tissue site to the means for delivering the electrical stimulation to the tissue site, wherein the means for electrically coupling the second lead defines a second opening to receive the second lead; wherein the first and second openings face different directions.

In another example, the disclosure is directed to a computer-readable medium comprising instructions that cause a programmable processor to perform any part of the techniques described herein.

The details of one or more examples are set forth in the accompanying drawings and the description below. Other features, objects, and advantages of the disclosure will be apparent from the description and drawings, and from the claims.

DETAILED DESCRIPTION

Figure 1:
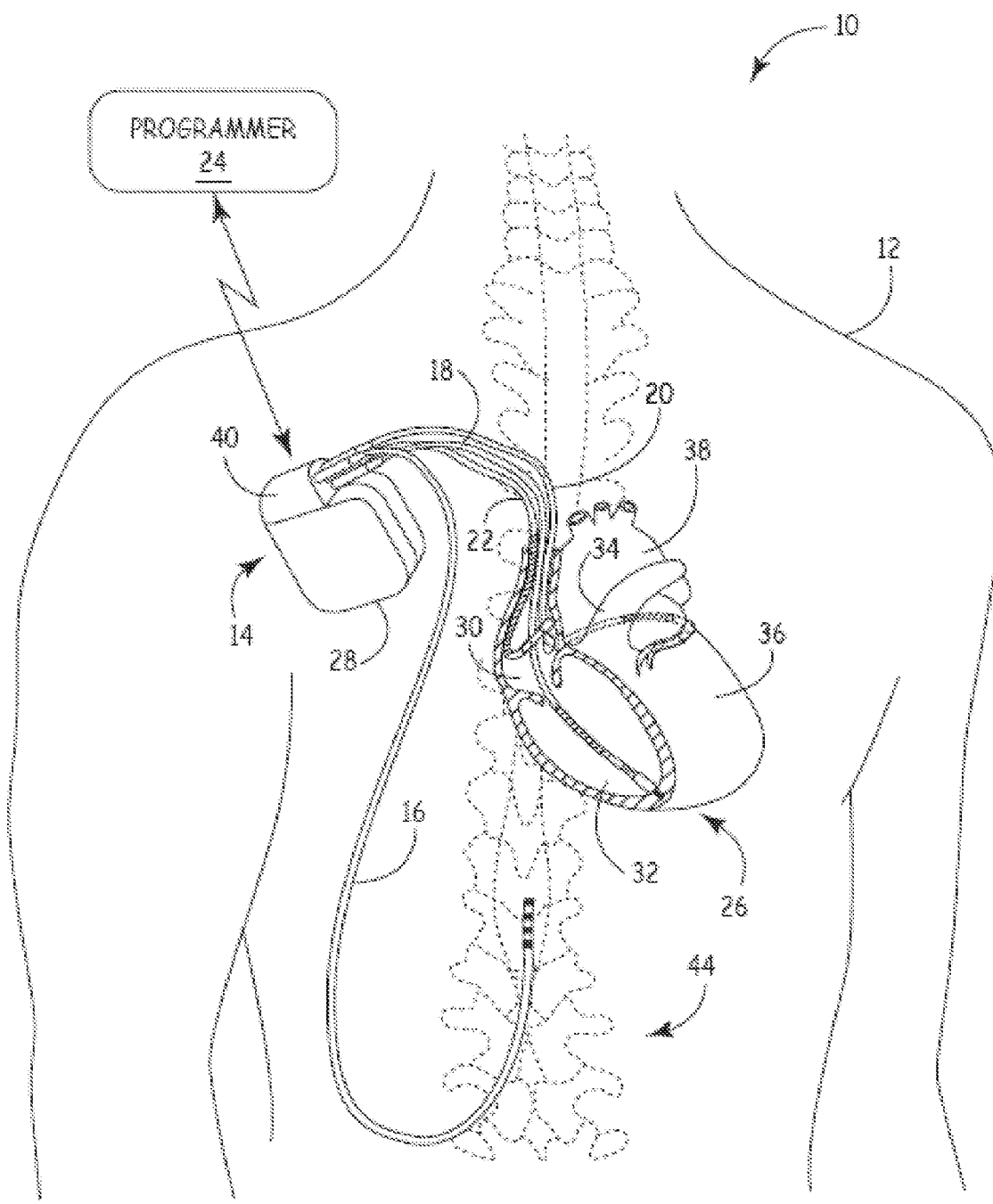
FIG. 1 is a conceptual diagram illustrating an example therapy system that includes an implantable medical device (IMD) configured to deliver electrical stimulation to a tissue site within a patient and deliver cardiac rhythm therapy management to a heart of the patient.

FIG. 1 is a conceptual diagram illustrating an example therapy system 10 that provides therapy to patient 12. Therapy system 10 includes implantable medical device (IMD) 14 and leads 16, 18, 20, 22, and programmer 24. As described in greater detail below, leads 16, 18, 20, 22 are mechanically and electrically coupled to IMD 14 via lead connection assembly 40, which may be connected housing 28 of IMD 14 as shown in FIG. 1. In some examples, housing 28 and lead connection assembly 40 are integrally formed, while in other examples, housing 28 and lead connection assembly 40 are separate components that are mechanically coupled together, e.g., via an adhesive, welding, interlocking components, and the like. In the example shown in FIG. 1, housing 28 and lead connection assembly 40 are be fabricated from any suitable biocompatible material, such as, but not limited to, titanium. Housing 28 and lead connection assembly 40 may be formed from the same material or different materials.

IMD 14 generates and delivers electrical stimulation to heart 26 via electrodes carried by one or more of leads 18, 20, 22 in order to manage a cardiac rhythm of heart 26. Accordingly, IMD 14 includes a first therapy module configured that generates at least one of pacing, cardioversion, or defibrillation therapy. The pacing therapy may include, for example, antitachyarrhythmia pacing (ATP) and pacing therapies designed to prevent ventricular tachycardia, ventricular fibrillation, atrial tachycardia, and/or atrial fibrillation. In some examples, IMD 14 delivers pacing pulses, but not cardioversion or defibrillation pulses, while in other examples, IMD 14 delivers cardioversion or defibrillation pulses, but not pacing pulses. In addition, in further examples, IMD 14 delivers pacing, cardioversion, and defibrillation pulses.

In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 26. Right atrial (RA) lead 22 extends through one or more veins and the vena cava, and into the right atrium 30 of heart 26. In other examples, IMD 14 delivers stimulation therapy to heart 26 by delivering stimulation to an extravascular tissue site in addition to or instead of delivering stimulation via electrodes of intravascular leads 18, 20, 22. An extravascular tissue site is outside of heart 26 and outside of arteries, veins, or other vasculature of patient 12.

IMD 14 may sense electrical signals attendant to the depolarization and repolarization of heart 26 via electrodes (not shown in FIG. 1) coupled to at least one of the leads 18, 20, 22. In some examples, IMD 14 provides pacing pulses to heart 26 based on the electrical signals sensed within heart 26. The configurations of electrodes used by IMD 14 for sensing and pacing may be unipolar or bipolar. IMD 14 may also provide defibrillation therapy and/or cardioversion therapy via electrodes located on at least one of the leads 18, 20, 22. IMD 14 may detect arrhythmia of heart 26, such as fibrillation of ventricles 32 and 36, and IMD 14 may be programmed to deliver a progression of therapies, e.g., pulses with increasing energy levels, until a fibrillation of heart 26 is stopped. IMD 14 may detect fibrillation employing one or more fibrillation detection techniques known in the art.

IMD 14 also comprises a second therapy module that generates electrical stimulation signals that are delivered to a tissue site within patient 12 via lead 16. In some examples, the tissue site may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some examples, delivery of electrical stimulation to a tissue site proximate a nerve or a nonmyocardial tissue site that may not be proximate a nerve may help modulate an autonomic nervous system of patient 12. In some examples, IMD 14 may deliver electrical stimulation therapy to a nerve of patient 12 via a lead implanted within vasculature (e.g., a blood vessel) of patient 12. In addition, in some examples, IMD 14 may deliver electrical stimulation that is delivered to peripheral nerves that innervate heart 26, or fat pads on heart 26 that may contain nerve bundles. The fat pads may be referred to as a nonvascular cardiac tissue site.

In the example shown in FIG. 1, IMD 14 delivers electrical stimulation to tissue proximate spinal cord 44 of patient 12 via lead 16. In other examples, IMD 14 may be coupled to two or more leads that may, for example, facilitate bilateral spinal cord stimulation of patient 12, although, in some examples, bilateral spinal cord stimulation may also be achieved with a single lead 16 positioned across the patient's midline. Although lead 16 is shown to be introduced into spinal cord 44 near the lumbar region in the example shown in FIG. 1, in other examples, lead 16 may be introduced into spinal cord 44 via the thoracic column. Electrodes of lead 16 may be positioned within an intrathecal space or epidural space of spinal cord 44, or, in some examples, adjacent nerves that branch off of spinal cord 44.

Delivery of electrical stimulation by IMD 14 to one or more target tissues sites, e.g., one or more target tissue sites proximate to a nerve, nerve site, cardiac fat pad, or an extravascular target tissue site that is proximate a nerve, may provide cardioprotective benefits to patient 12. For example, deliver of electrical stimulation to a tissue site proximate a nerve of patient 12 may help treat heart failure. In addition, delivery of electrical stimulation to a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 26 or cardiac muscle trauma. In addition, delivery of electrical stimulation by IMD 14 may complement antitachycardia therapy (e.g., antitachycardia pacing, cardioversion or defibrillation) by IMD 14 or provide back-up therapy to the cardiac rhythm therapy provided by the first therapy module.

Stimulation of spinal cord 44 or nerves branching therefrom by IMD 14 may help prevent or mitigate occurrences of tachyarrhythmias and may reduce the level of aggressiveness of the cardiac therapy, such as pacing, cardioversion or defibrillation, delivered by IMD 14. In this way, IMD 14 may operate to help prevent arrhythmias of heart 26 of patient 12, as well as to terminate detected arrhythmias. In other examples, IMD 14 may provide electrical stimulation therapy of a parasympathetic nerve, such as a vagus nerve, of patient 12. Stimulation of a parasympathetic nerve of patient 12 may help slow intrinsic rhythms of heart 26, which may complement antitachyarrhythmia therapy also delivered by IMD 14.

In some examples, depending upon the stimulation target, the delivery of electrical stimulation by IMD 14 via lead 16 may also mitigate perceptible discomfort generated from the delivery of pacing pulses or cardioversion/defibrillation shocks by IMD 14. For example, if IMD 14 delivers electrical stimulation to spinal cord 44 of patient 12, the neurostimulation may produce paresthesia, which may help reduce the discomfort felt by patient 12 from the delivery of pacing pulses or cardioversion/defibrillation shocks by IMD 14.

In other examples, electrodes of lead 16 may be positioned to deliver electrical stimulation to any other suitable nerve, organ, muscle or muscle group in patient 12, which may be selected based on, for example, a therapy program or regimen selected for a particular patient. In some examples, IMD 14 may deliver electrical stimulation to other sympathetic or parasympathetic nerves, baroreceptors, cardiac fat pads, or the carotid sinus or a cardiac branch of the vagal trunk of patient 12 in order to facilitate the delivery of cardiac rhythm therapy by IMD 14, as previously described.

In some examples, IMD 14 may also be referred to as a signal generator, stimulation generator or an electrical stimulator. In some examples, lead 16 may also carry one or more sense electrodes to permit IMD 14 to sense electrical signals within patient 12. In the example of FIG. 1, IMD 14 has been implanted in patient 12 at a location that allows leads 18, 20, 22 to be positioned within heart 26, and allows lead 16 to be positioned proximate spinal cord 44. For example, IMD 14 may be subcutaneously or submuscularly implanted in the body of a patient 12 (e.g., in a chest cavity, lower back, lower abdomen, or buttocks of patient 12).

In the example shown in FIG. 1, a single IMD 14 provides both cardiac rhythm therapy and electrical stimulation therapy other than cardiac rhythm therapy. Accordingly, the components for generating and delivering the pacing, cardioversion and/or defibrillation therapy via leads 18, 20, and 22, and generating and delivering the electrical stimulation therapy to a target tissue site via lead 16 may be substantially contained within outer housing 28 of IMD 14. As described in further detail below, lead connection assembly 40 includes a first electrical connector that mechanically couples at least one of the leads 18, 20, 22 to IMD 14 and electrically connects at least one of the leads 18, 20, 22 to the first therapy module within housing 28. Lead connection assembly 40 further includes a second electrical connector that mechanically couples lead 16 to IMD 14 and electrically connects lead 16 to the second therapy module within housing 28. For example, a proximal end of each of leads 16, 18, 20, 22 may be both electrically and mechanically coupled to lead connection assembly 40 of IMD 14 either directly or indirectly (e.g., via a lead extension). Electrical conductors disposed in the respective lead body may electrically connect stimulation electrodes (and sense electrodes, if present) of leads 16, 18, 20, 22 to either the first or second therapy modules within IMD 14 via lead connection assembly 40. Lead connection assembly 40 may also be referred to as a header or a connector block.

While the disclosure primarily describes leads as being directly connected to lead connection assembly 40, in other examples, leads, such as leads 16, 18, 20, 22, may be indirectly mechanically and electrically connected to lead connection assembly 40 via one or more lead extensions. A lead extension may effectively elongate a lead. In addition, in some examples, a bifurcated or trifurcated lead extension may be useful for mechanically and electrically connecting more than one lead to a common electrical connector of lead connection assembly 40.

The first and second electrical connectors of lead connection assembly 40 are configured to mate with a proximal portion of a corresponding lead or lead extension. The first and second electrical connectors of lead connection assembly 40 are configured to help prevent electrical stimulation from being inadvertently delivered to an incorrect tissue site within patient 12. For example, the first electrical connector may be configured such that it is substantially incompatible with lead 16 in order to prevent lead 16 from inadvertently being electrically connected to the first therapy module. Similarly, the second electrical connector may be configured such that it is substantially incompatible with one or more of leads 18, 20, 22 in order to prevent the one or more of leads 18, 20, 22 from being electrically connected to the second therapy module. The incompatibility between lead 16 and the first electrical connector of lead connection assembly 40 and between leads 18, 20, 22 and the second electrical connector of lead connection assembly 40 may be achieved via different techniques, such as incompatible physical characteristics (e.g., incompatible geometries), incompatible electrical contact arrangements, and/or incompatible sizes, as described in further detail below.

When leads 18, 20, 22 are properly connected to the first therapy module within IMD 14, the first therapy module of IMD 14 delivers at least one of pacing, cardioversion or defibrillation stimulation to heart 26 by implantable medical leads 18, 20, 22, and more particularly, via one or more stimulation electrodes carried by leads 18, 20, 22. Similarly, when lead 16 is properly connected to the second therapy module within IMD 14, the second therapy module delivers electrical stimulation (e.g., in the form of electrical pulses or a continuous signal) to a nonmyocardial or a nonvascular cardiac tissue site. In the example shown in FIG. 1, the second therapy module delivers electrical stimulation to a tissue site proximate spinal cord 44 via one or more stimulation electrodes carried by lead 16.

In some examples, IMD 14 also includes one or more housing electrodes, which may be formed integrally with an outer surface of hermetically-sealed housing 28 of IMD 14 or otherwise coupled to housing 28. In some examples, the housing electrode may be defined by an uninsulated portion of an outward facing portion of housing 28. Other divisions between insulated and uninsulated portions of housing 70 may be employed to define two or more housing electrodes. In some examples, such as the example shown in FIG. 1, the housing electrode may comprise substantially all of housing 28. In other examples, one or more electrodes may be embedded into an insulating casing that surrounds the outer surface of housing 28 or otherwise attached to outer housing 28 of IMD 14. Any of the electrodes of leads 16, 18, 20, 22 may be used for unipolar sensing or stimulation in combination with the one or more housing electrodes.

As shown in FIG. 1, therapy system 10 also includes programmer 24. In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with IMD 14. For example, the user may interact with programmer 24 to retrieve physiological or diagnostic information from IMD 14. A user may also interact with programmer 24 to program IMD 14, e.g., select values for operational parameters for one or more of the stimulation therapies delivered by IMD 14. For example, the user may use programmer 24 to retrieve information from IMD 14 regarding the rhythm of heart 26, trends therein over time, or tachyarrhythmia episodes. As another example, the user may use programmer 24 to retrieve information from IMD 14 regarding other sensed physiological parameters of patient 12, such as electrical depolarization/repolarization signals from heart 26 (referred to as "electrogram" or EGM), intracardiac or intravascular pressure, activity, posture, respiration, or thoracic impedance. As another example, the user may use programmer 24 to retrieve information from IMD 14 regarding the performance or integrity of IMD 14 or other components of system 10 corresponding to the first stimulation therapy, such as leads 16, 18, 20, and 22, or a power source of IMD 14.

The user may use programmer 24 to program a therapy progression, select electrodes used to deliver defibrillation pulses, select waveforms for the defibrillation pulse, or select or configure a fibrillation detection algorithm for IMD 14. The user may also use programmer 24 to program aspects of other therapies provided by IMD 14, such as cardioversion, pacing or other electrical stimulation therapies. For example, with the aid of programmer 24, a user may select therapy parameters for the pacing, cardioversion, and/or defibrillation therapy delivered by leads 18, 20, 22, and/or the stimulation therapy delivered by lead 16. The stimulation therapy parameters may include, for example, an electrode combination, a current or voltage amplitude, and a frequency of stimulation signals to be delivered to patient 12, and, in the case of stimulation pulses, a pulse width and a pulse rate.

An electrode combination may include a selected subset of one or more electrodes located on implantable leads 16, 18, 20, 22 that are coupled to IMD 14. The electrode combination may also refer to the polarities of the electrodes in the selected subset. By selecting values for a slew rate, amplitude, frequency (e.g., pulse rate in the case of stimulation pulses), and pulse duration (e.g., pulse width in the case of stimulation pulses), the clinician can attempt to generate an efficacious therapy for patient 12 that is delivered via the selected electrode subset. In addition, at least with respect to lead 16, by selecting particular electrode combinations, a clinician may target particular anatomic structures within patient 12.

In some examples, the user may activate certain features of IMD 14 by entering a single command via programmer 24, such as depression of a single key or combination of keys of a keypad or a single point-and-select action with a pointing device. With the aid of programmer 24 or another computing device, a user may select values for therapy parameters for the second stimulation therapy generated and delivered by IMD 14. The values for the therapy parameters of the second stimulation therapy may be organized into a group of parameter values referred to as a "therapy program" or "therapy parameter set." "Therapy program" and "therapy parameter set" are used interchangeably herein.

Programmer 24 may communicate with IMD 14 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 14 implant site in order to improve the quality or security of communication between IMD 14 and programmer 24.

Figure 2:
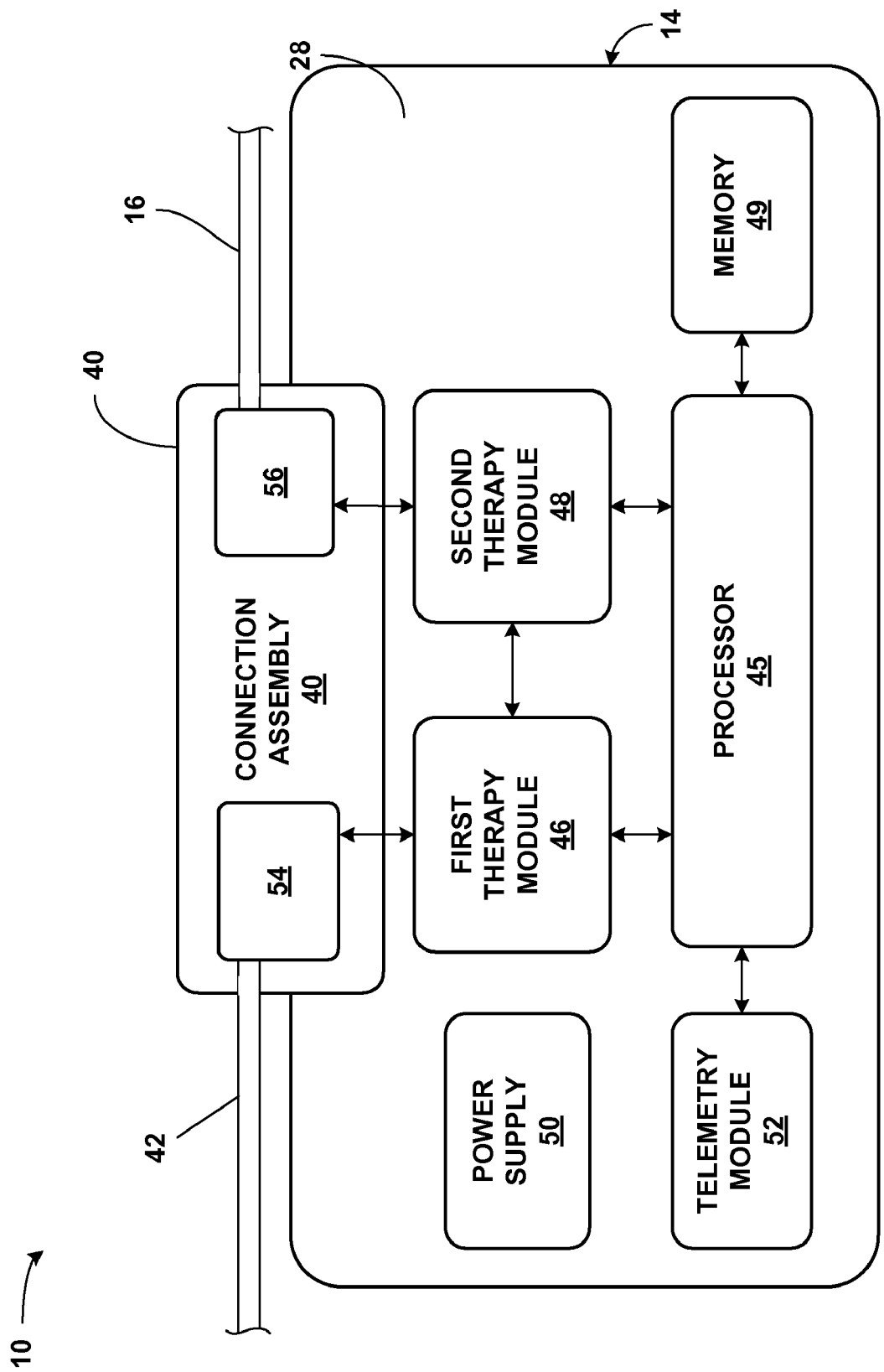
FIG. 2 is a functional block diagram illustrating the IMD of FIG. 1.

FIG. 2 is a functional block diagram illustrating example therapy system 10 including IMD 14, lead connection assembly 40, lead 42, and lead 16. Lead 42 may be any one or more of leads 18, 20, 22 or a lead extension electrically and mechanically coupled to one or more of leads 18, 20, 22. Although FIG. 2, as well as FIGS. 3-7, illustrate lead connection assembles configured to receive two leads, in other examples, lead connection assemblies in accordance with the disclosure may be configured to receive any suitable number of leads, such as one, two, three, four or more.

As shown in FIG. 2, IMD 14 includes processor 45, first therapy module 46, second therapy module 48, memory 49, power supply 50, and telemetry module 52. Memory 49 may include computer-readable instructions that, when executed by processor 45, cause processor 45 to perform various functions attributed to processor herein. Memory 49 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 45 may include any one or more of a microprocessor, a controller, a digital signal processor (DSP), an application specific integrated circuit (ASIC), a field-programmable gate array (FPGA), or equivalent discrete or integrated logic circuitry. In some examples, processor 45 may include multiple components, such as any combination of one or more microprocessors, one or more controllers, one or more DSPs, one or more ASICs, or one or more FPGAs, as well as other discrete or integrated logic circuitry. The functions attributed to processor 45 herein may be embodied as software, firmware, hardware or any combination thereof Processor 45 may control first and second therapy modules 46, 48, respectively, to generate and deliver stimulation therapy to patient 12 according to a selected one or more of therapy programs, which may be stored in memory 49. Specifically, processor 45 may control the and second therapy modules 46, 48, respectively, to generate electrical signals with the amplitudes, pulse widths, frequency, or electrode polarities specified by the selected one or more therapy programs.

First therapy module 46 and second therapy module 48 may each include signal generators in order to generate the stimulation signals for delivery to patient 12. First therapy module 46 may be configured generate and deliver electrical stimulation signals of a first stimulation therapy type to patient 12 via lead 42. For example, first therapy module 46 may generate and deliver at least one of pacing, cardioversion or defibrillation therapy to heart 26 of patient 12 via lead 42. If first therapy module 46 is configured to generate and deliver defibrillation pulses to heart 26, first therapy module 46 may include a high voltage charge circuit and a high voltage output circuit. If first therapy module 46 is configured to generate and deliver pacing pulses to heart 26, processor 45 may include pacer timing and control module, which may be embodied as hardware, firmware, software, or any combination thereof. The pacer timing and control module may comprise a dedicated hardware circuit, such as an ASIC, separate from other processor 45 components, such as a microprocessor, or a software module executed by a component of processor 45, which may be a microprocessor or ASIC. The pacer timing and control module may be used by processor 45 to time the delivery of pacing pulses to heart 26.

Second therapy module 48 may be configured to generate and deliver electrical stimulation signals of a second stimulation therapy type to patient 12 via lead 16, where the second stimulation therapy type is different than the first stimulation therapy type. For example, second therapy module 48 may generate and deliver electrical stimulation therapy (e.g., neurostimulation) to a nonmyocardial tissue site (e.g., a tissue site proximate a nerve and/or an extravascular tissue site not proximate a nerve) or a nonvascular cardiac tissue site (e.g., a cardiac fat pad) via lead 16.

First therapy module 46 and second therapy module 48 may be electrically coupled to one or more electrodes of the respective lead 42, 16 via conductors of the respective lead 42, 16, or, in the case of a housing electrode, via an electrical conductor disposed within housing 28 of IMD 14. Lead 42 may be, for example, any one of leads 18, 20, 22 of therapy system 10 shown in FIG. 1. In some examples, first therapy module 46 is configured to receive leads 18, 20, 22, rather than a single lead 42, as shown in FIG. 2. In some examples, first therapy module 46 may deliver defibrillation shocks to heart 26 via at least two electrodes coupled to lead 42 or housing 28. First therapy module 46 may deliver pacing pulses via the housing electrode, ring electrodes coupled to lead 42, respectively, and/or helical electrodes of lead 42. In some examples, first therapy module 46 may deliver pacing, cardioversion, or defibrillation stimulation in the form of electrical pulses. In other examples, first therapy module 46 may deliver one or more of these types of stimulation in the form of other signals, such as sine waves, square waves, or other substantially continuous time signals.

Second therapy module 48 may be configured to generate and deliver second electrical stimulation therapy to a nonmyocardial tissue site, such as, e.g., an extravascular tissue site and/or tissue site proximate to a nerve, e.g., spinal cord 44, via at least two electrodes coupled to lead 16 and/or housing 28.

First and/or second therapy module 46, 48 may include a switch module, and processor 45 may use the switch module to select, e.g., via a data/address bus, which of the available electrodes of housing 28 and leads 16, 42 are used to deliver electrical stimulation. The switch module may include a switch array, switch matrix, multiplexer, or any other type of switching device suitable to selectively couple stimulation energy to selected electrodes. In other examples, however, first and/or second therapy module 46, 48 may independently deliver stimulation to one or more electrodes without a switch matrix.

In some examples first and second therapy modules 46, 48, respectively, may share one or more components utilized to operate as described herein. For example, in some cases, first therapy module 46 and second therapy module 48 may share a switch module. In addition, in some examples, first and second therapy modules 46, 48, respectively, may include components dedicated to only a single respective therapy module. For example, first and second therapy modules 46, 48, respectively, may have respective processors and/or memories.

Although not shown in FIG. 2, IMD 14 may also include a sensing module that monitors signals from at least one of the electrodes of leads 16, 42 and/or housing 28 in order to monitor electrical activity of heart 26, e.g., via an EGM signal. In some examples, the sensing module may include one or more sensing channels, each of which may comprise an amplifier. Under the control of processor 45, the switch module of the sensing module may couple the outputs from the selected electrodes to one of the sensing channels. The sensed electrical activity of heart 26 may be used to control the timing of the delivery of pacing, cardioversion or defibrillation shocks by first therapy module 46. For example, processor 46 may employ any suitable arrhythmia detection methodologies in order to detect an arrhythmia based on electrical cardiac signals sensed by the sensing module, and the detection of an arrhythmia may be used to control the delivery of defibrillation shocks by first therapy module 46, e.g., to attempt to terminate the detected arrhythmia.

Telemetry module 52 includes any suitable hardware, firmware, software or any combination thereof for communicating with another device, such as programmer 24 (FIG. 1). Under control of processor 45 of IMD 14, telemetry module 52 may receive downlink telemetry from and send uplink telemetry to programmer 24 with the aid of an antenna, which may be internal and/or external. IMD 14 may provide the data to be uplinked to programmer 24 and the control signals for the telemetry circuit within telemetry module 52 e.g., via an address/data bus. In some examples, telemetry module 52 may provide received data to a processor of IMD 14 via a multiplexer.

The various components of IMD 14 may be coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12.

As previously described, IMD 14 may be mechanically coupled to leads 16, 42 and electrically coupled to electrodes of leads 16, 42 via lead connection assembly 40. As shown in FIG. 2, lead connection assembly 40 includes first electrical connector 54 and second electrical connector 56, which are configured to receive leads 42, 16, respectively. When lead 42 is properly connected to first electrical connector 54, electrical stimulation generated by first therapy module 46 may be conducted from first therapy module 46 to heart 26 of patient 12 via conductors and electrodes of lead 42. Similarly, when lead 16 is properly connected to second electrical connector 56, electrical stimulation generated by second therapy module 48 may be conducted from second therapy module 48 to spinal cord 44 (or another tissue site) via conductors and electrodes of lead 16. In this manner, IMD 14 may be configured to deliver both two different types of electrical stimulation therapy to patient 12.

Lead connection modules illustrated and described herein with respect to FIGS. 2-7 include two electrical connectors for ease of illustration and description. In other examples, lead connection modules described herein may include any suitable number of electrical connectors to electrically couple any suitable number of leads to therapy modules 46, 48. For example, as shown in FIG. 1, therapy system 10 may include four leads 16, 18, 20, 22, whereby three leads 18, 20, 22 are used to deliver cardiac rhythm therapy to heart 26 of patient 12. Accordingly, in some examples, lead connection assembly 40 may include additional electrical connectors that are configured to receive additional leads of therapy system 10, e.g., such that lead connection assembly 40 may electrically couple electrodes of leads 18, 20, 22 to first therapy module 46 and/or electrodes of an additional lead to therapy module 48. In other examples, one or both electrical connectors 54, 56 may be configured to receive more than one lead.

First electrical connector 54 and second electrical connector 56 may be any suitable type of electrical connector capable of electrically and mechanically coupling lead 42 and lead 16, respectively, to IMD 14. For example, first electrical connector 54 and second electrical connector 56 may each be configured as receptacles configured to receive a proximal end of the respective lead 42, 16 (or a lead extension). In some examples, the proximal end of a lead (or lead extension) may be physically secured in the corresponding electrical connector receptacle via a set screw, while in other examples, the proximal end of each lead (or lead extension) may mate with the receptacle in a self-securing manner. In some examples, first and/or second electrical connectors 54 and 56 are Bayonet Neill Concelman (BNC) electrical connectors or have configurations similar to BNC electrical connectors, which are physically configured to mate with the respective lead 42, 16. In addition, in some examples, first and/or second electrical connectors 54 and 56 are threaded Neill Concelman (TNC) type electrical connectors or have configurations (e.g., bayonet mount style) similar to TNC electrical connectors, which are configured to physically mate with and receive leads 42, 16 in a threaded configuration. In other examples, first and/or second electrical connectors 54 and 56 are connected to leads 42, 16 without the aid of a set screw, such as with the aid of a lever that pushes leads 42, 16 into physical and electrical connection with electrical contacts within the respective electrical connectors 54, 56.

In some examples, during implantation of therapy system 10 in patient 12, a clinician may inadvertently attempt to introduce lead 16 into first electrical connector 54 and/or attempt to introduce lead 42 may inadvertently introduced into second electrical connector 56. In some cases, it may be undesirable for lead 16 to deliver electrical stimulation from first therapy module 46 to a nonmyocardial tissue site or a nonvascular cardiac tissue site, e.g., a tissue site proximate a nerve or an extravascular tissue site that may not be proximate a nerve. In addition, it may be undesirable for lead 42 to deliver electrical stimulation generated by second therapy module 48 to heart 26.

In some examples, the delivery of electrical stimulation therapy that is configured for delivery to spinal cord 44, or another tissue site other than vascular tissue of heart 26, e.g., another tissue site proximate a nerve or an extravascular tissue site, may cause one or more undesirable physiological responses if delivered heart 26. For example, the stimulation therapy generated by second therapy module may include second electrical stimulation signals including a frequency ranging from approximately 1 Hertz (Hz) to approximately 100 Hz, such as, approximately 10 Hz to approximately 100 Hz. The delivery of electrical stimulation signals having such a frequency to heart 26 may induce an arrhythmia, such as a ventricular fibrillation, which may be undesirable.

In general, the configuration of lead connection assembly 40 may provide a safeguard against the unintended delivery of electrical stimulation signals generated by second therapy module 48 to heart 26 of patient 12 via lead 42. In some examples, second electrical connector 56 of connector assembly 40 may be physically incompatible with lead 42, e.g., based on the relative geometry or sizes of second electrical connector 56 and lead 42. In some examples, the incompatibility substantially prevents lead 42 from being introduced into the receptacle defined by second electrical connector 56, e.g., because of size or geometrical constraints.

In other examples, in addition to or instead of the size or geometrical constraints, second electrical connector 56 and lead 42 may be substantially electrically incompatible. For example, the configuration of second electrical connector 56 may prevent at least some of the electrodes of lead 42 from being electrically connected to second electrical connector 56. This may be accomplished, for example, by different arrangements of electrical contacts on lead 42 and within second electrical connector 56 or with an electrical component other than the electrical contacts that electrically connects to a corresponding portion of the respective lead 16, 42. In some examples, a lack of an electrical connection between the electrical component of the electrical connector 54, 56 and the respective lead 42, 16 may substantially prevent therapy modules 46, 48 from delivering therapy via the electrodes of the respective lead 42, 16. In this way, the incompatibility between second electrical connector 56 and lead 42 may help prevent lead 42 from being inadvertently electrically coupled to second therapy module 48 via second electrical connector 56.

In addition, in some examples, first electrical connector 54 of connector assembly 40 may be incompatible with lead 16 in order to provide a safeguard against the unintended delivery of electrical stimulation signals generated by first therapy module 46 to a tissue site within patient 12 via lead 16. For example, first electrical connector 54 may define a receptacle that is configured to prevent lead 16 from being introduced into the receptacle, e.g., because of size or geometrical constraints. In other examples, in addition to or instead of the size or geometrical constraints, the incompatibility between first electrical connector 54 and lead 16 prevents at least some of the electrodes of lead 16 from being electrically connected to first electrical connector 54. This may be referred to herein as electrical incompatibility.

Figure 4:
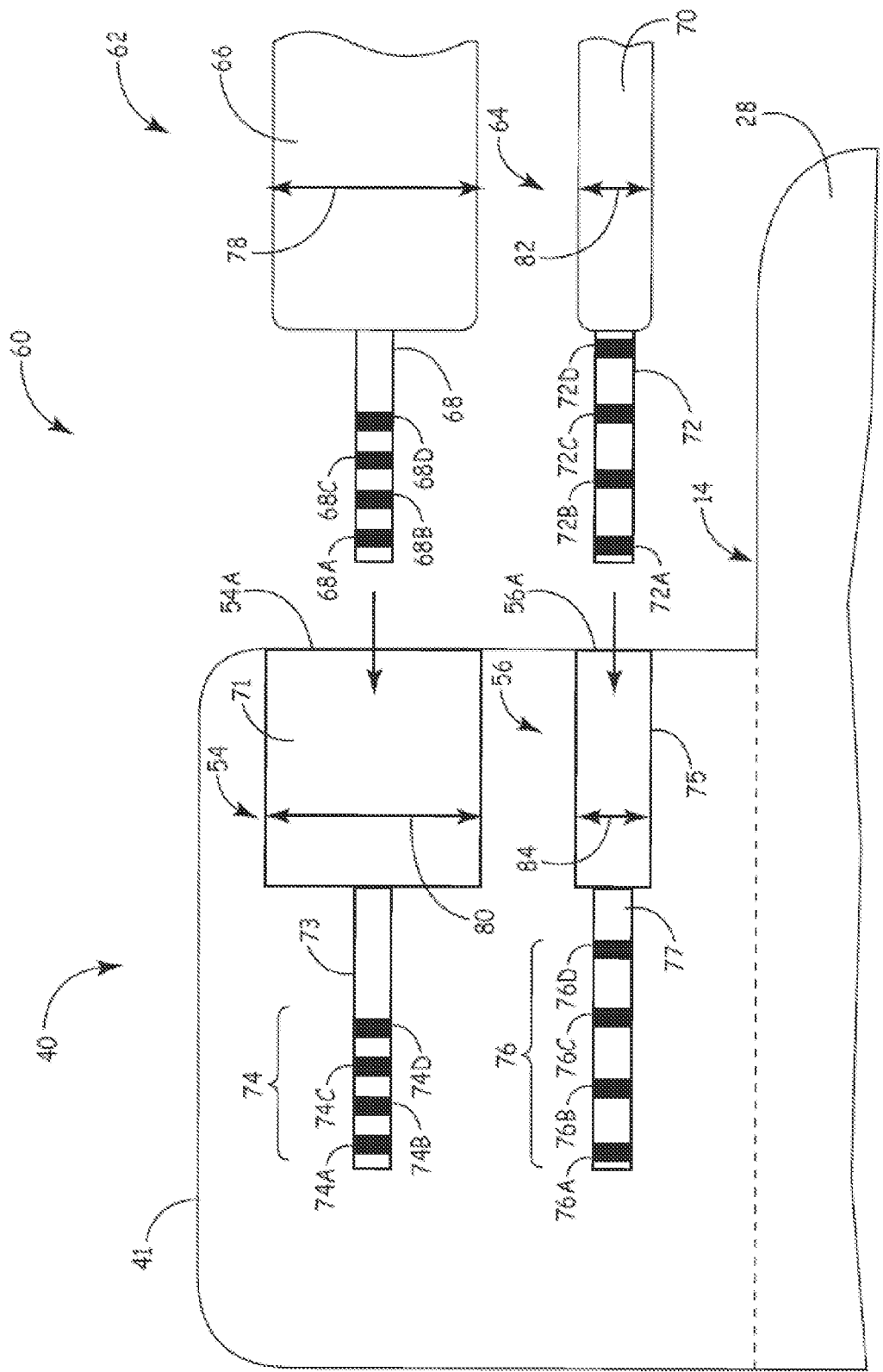
FIG. 4 is a conceptual diagram illustrating a cross-sectional view of a portion of the example therapy system of FIG. 3.

In addition to or instead of achieving lead 42 incompatibility with second electrical connector 56 and/or lead 16 incompatibility with first electrical connector 54 via different geometrical or sizes, or different electrical contact arrangements, which are described in further detail with respect to FIG. 4, leads 16, 42 and electrical connectors 54, 56 may be marked with a visible identifier that helps a user associate leads 42, 16 with the proper electrical connector 54, 56, respectively. In some examples, at least a portion of lead 42 may be marked with a first color (e.g., via a colored band embedded or otherwise incorporated or attached to lead 42) and first electrical connector 54 may also be marked with the first color. As an example, first electrical connector 54 may have a color band within or outside of a perimeter of an opening configured to receive lead 42. The color coding may indicate to a user that first lead 42 should be introduced into first electrical connector 54. Thus, during assembly of therapy system 10, the user may match the color coding on lead 42 with the color coding on lead connection assembly 40 in order to electrically couple lead 42 to the proper therapy module. Similarly, at least a portion of lead 16 may be marked with a second color and second electrical connector 54 may also have portion with the second color. Alphanumeric identifiers, symbolic identifiers (e.g., geometric symbols) or other types of visible identifiers may also be used to associate leads 16, 42 with the respective electrical connectors 56, 54.

In the example shown in FIG. 2, electrical connectors 54, 56 define openings that permit leads 42, 16, respectively, to extend away from housing 28 of IMD 14 in substantially different directions. In particular, in the example shown in FIG. 2, leads 42, 46 extend from housing 28 in substantially opposite directions. In other examples, leads 42, 46 may extend from housing 28 in any suitable directions that are different from each other, such as, but not limited to orthogonal directions. As described with respect to FIG. 8, this configuration of lead connection assembly 40 may be more conducive to implanting therapy system 10 in patient 12.

Figure 3:
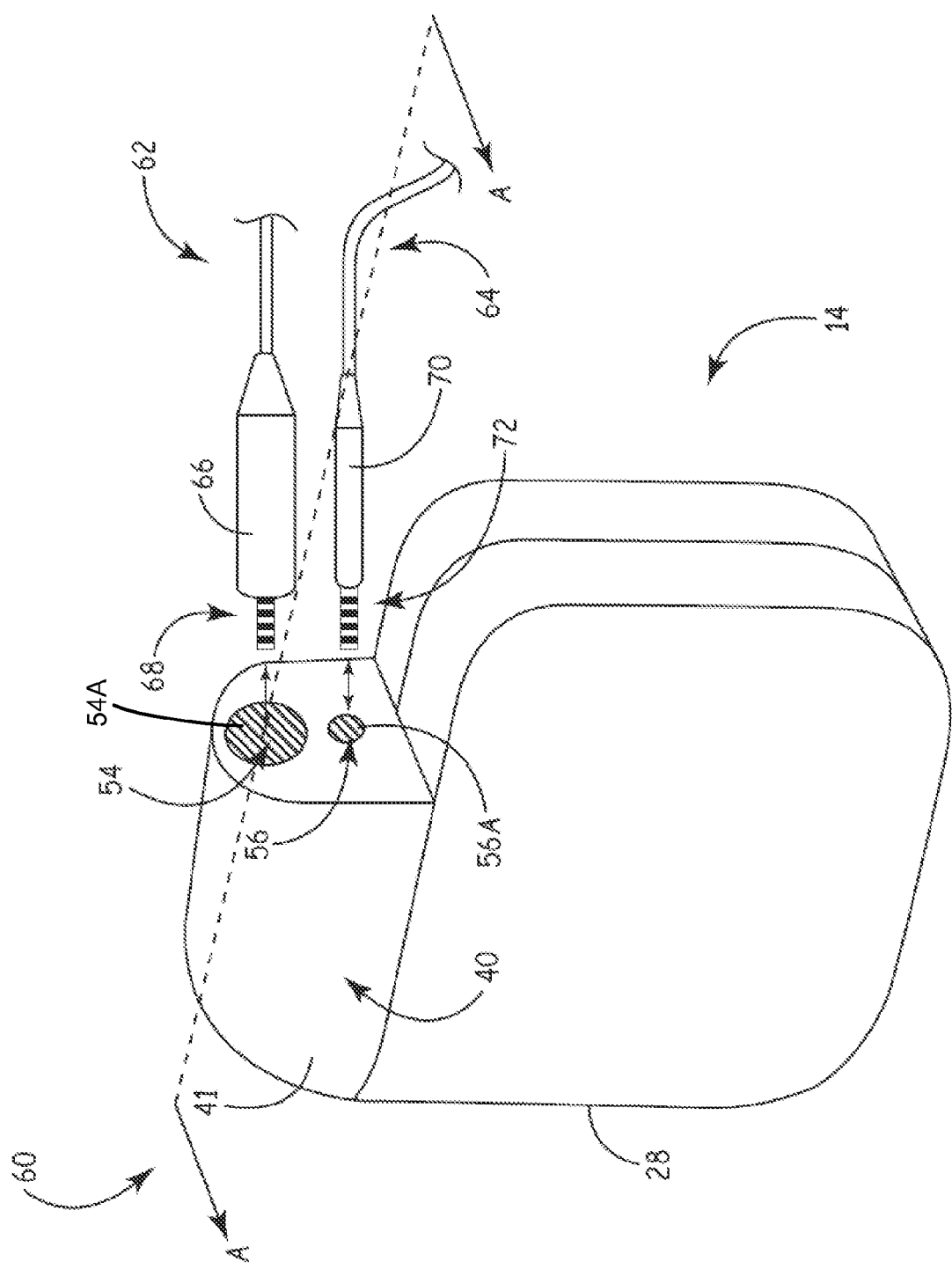
FIG. 3 is a conceptual diagram illustrating a perspective view of an example therapy system.

FIG. 3 is a conceptual diagram illustrating a perspective view of example therapy system 60, which includes IMD 14, lead connection assembly 40, first lead 62, and second lead 64. IMD 14 and lead connection assembly 40 are described above with respect to FIGS. 1 and 2. Lead 62 may be configured to deliver electrical stimulation from first therapy module 46 (FIG. 2) to heart 26 (FIG. 1) of patient 12, and lead 64 may be configured to deliver electrical stimulation from second therapy module 48 (FIG. 2) to a nonmyocardial tissue site or a nonvascular cardiac tissue site within patient 12. Thus, in some examples, first lead 62 may be the same or similar to that of one or more of leads 18, 20, 22 of FIG. 1 and second lead 64 may be the same or similar to that of lead 16 of FIG. 1.

FIG. 3 illustrates an example lead connection assembly 40 in which first and second electrical connectors 54, 56, respectively, have one or more features that help prevent the inadvertent delivery of electrical stimulation from second therapy module 48 (FIG. 2) to heart 26 of patient 12. That is, first and second electrical connectors 54, 56, respectively, have one or more features that help prevent first lead 62 from being electrically coupled to second therapy module 48 via second electrical connector 56.

Lead connection assembly 40 is configured to connect first and second leads 62, 64 to first and second therapy modules 46, 48, respectively, enclosed within housing 28 of IMD 14. Leads 62, 64 may be introduced into openings 54A, 56A, respectively, defined by housing 41 of lead connection assembly 40. In FIG. 3, first lead 62 and second lead 64 are disconnected from lead connection assembly 40, but aligned with respective openings 54A, 56A. In the example shown in FIG. 3, first electrical connector 54 is configured to electrically and mechanically couple first lead 62 to first therapy module 46, such that cardiac rhythm therapy generated by first therapy module 46 may be delivered to heart 26 of patient 12 via one or more electrodes of first lead 62. Second electrical connector 56 is configured to electrically and mechanically couple second lead 64 to second therapy module 48 such that electrical stimulation signals generated by second therapy module 48 may be delivered to spinal cord 44 of patient 12 via one or more electrodes of second lead 64.

As shown in FIG. 3, first electrical connector 54 and second electrical connector 56 may be receptacle-type electrical connectors. For example, each electrical connector 54, 56 may define a recess in housing 41 lead connection assembly 40 that is configured to receive a proximal portion of the respective lead 62, 64. In the example shown in FIG. 3, the proximal portion of first lead 62 includes first plug member 66 and first electrical contact portion 68. First electrical contact portion 68 includes a first set of electrical contacts that are electrically coupled to electrodes of lead 62 via conductors within a lead body of lead 62. At least a portion of first electrical contact portion 68 may be introduced into first electrical connector 54 in a manner that electrically couples electrodes of lead 62 to first therapy module 46 (FIG. 2) via the first set of electrical contacts. Similarly, second lead 64 includes second plug structure 70 and second electrical contact portion 72. Second electrical contact portion 72 and at least a portion of second plug structure 70 may be introduced into second electrical connector 56 in a manner that electrically couples electrodes of second lead 64 to second therapy module 48 (FIG. 2) via a second set of electrical contacts that are located on second electrical contact portion 72.

In the example shown in FIG. 3, second electrical connector 56 of lead connection assembly 40 is incompatible with first lead 62. For example, as described in greater detail with respect to FIG. 4, the physical dimensions of second electrical connector 56 and/or first plug member 66 and/or first electrical contact portion 68 may substantially discourage first lead 62 from being introduced into opening 56A of second electrical connector 56. For example, in the example shown in FIG. 3, first plug member 66 of first lead 62 has a larger cross-sectional size (measured along a direction substantially orthogonal to a longitudinal axis of lead 62) than an opening 56A, such that first lead 62 may not be easily introduced into second electrical connector 56. In this way, first lead 62 may be considered to be physically incompatible with second electrical connector 56.

The difference in size between first plug member 66 of first lead 62 and opening 56A of second electrical connector 56 may both visually and tactilely indicate to a user, such as a clinician, that lead 62 is not intended to be introduced into second electrical connector 56. For example, the user may be alerted to the incompatibility between first lead 52 and second electrical connector 56 based on a visual assessment of the different sizes, and, in some examples, as well as based on the different visual indicia on lead 62 and electrical connector 56. As another example, the user may be alerted to the incompatibility between first lead 52 and second electrical connector 56 based on the resistance first lead 62 exerts when the user attempts to introduce first lead 62 into second electrical connector 56.

FIG. 4 is a conceptual diagram illustrating a cross-sectional view of a portion of system 60 of FIG. 3. In particular, FIG. 4 illustrates a cross-sectional view of IMD 14, electrical connector assembly 40, first lead 62, and second lead 64 taken along line A-A in FIG. 3. First electrical connector 54 of lead connection assembly 40 may include first portion 71 and second portion 73, which defines a plurality of electrical contacts 74A-74D (collectively "electrical contacts 74"). Electrical contacts 74 are electrically coupled to first therapy module 46 (not shown), e.g., via conductive elements that extend between electrical contacts 74 and first therapy module 46. Opening 54A defined by housing 41 of lead connection assembly 40 provides access to first portion 71 and second portion 73 of first electrical connector 54, through which lead 62 may be introduced. First portion 71 and second portion 73 may define, for example, a receptacle of first electrical connector 54.

Second electrical connector 56 of lead connection assembly 40 may include first portion 75 and second portion 77, which may define a receptacle of second electrical connector 56. Second portion 77 of second electrical connector 56 includes a plurality of electrical contacts 76A-76D (collectively "electrical contacts 76") that are electrically coupled to second therapy module 48 (not shown), e.g., via conductive elements that extend between electrical contacts 76 and second therapy module 48. Opening 56A defined by housing 41 of lead connection assembly 40 provides access to first portion 75 and second portion 77 of second electrical connector 56, through which lead 64 may be introduced.

First lead 62 is compatible with first electrical connector 54. For example, the physical dimensions of first electrical connector 54 permit first electrical contact portion 68 and at least a portion of first plug member 66 of first lead 62 to be introduced into through openings 54A and into first electrical connector 54. In the example shown in FIG. 4, diameter 78 of first plug member 66 is substantially equal to or less than diameter 80 of first portion 71 of first electrical connector 54. Accordingly, when properly inserted, second portion 73 of first electrical connector 54 may receive first electrical contact portion 68 in a manner that electrically couples first lead 62 to first therapy module 46. That is, when lead 62 is properly introduced into first electrical connector 54, electrical contacts 68A-68D of lead 62 may contact electrical contacts 74A-74D, respectively, of second portion 74 of first electrical connector 54. In some examples, electrical contacts 68A-68D and electrical contacts 74A-74D have substantially similar surface areas, and when lead 62 is properly introduced into first electrical connector 54, electrical contacts 68A-68D and electrical contacts 74A-74D substantially align such that a majority of the surface areas (e.g., greater than 75%) of each of the electrical contacts 68A-68D is in contact with a majority of the surface area of a respective electrical contact 74A-74D.

As previously indicated, electrical contacts 68A-68D of lead 62 may be electrically coupled to a respective stimulation or sensing electrode of lead 62 via conductors within a lead body of lead 62. Thus, aligning electrical contacts 68A-68D of lead 62 with electrical contacts 74A-74D of first electrical connector 54 may electrical connect the electrodes of lead 62 with first therapy module 46, which is electrically connected to electrical contacts 74A-74D.

Second lead 64 is compatible with second electrical connector 56. For example, the physical dimensions of second electrical connector 56 permit second electrical contact portion 72 and at least a portion of second plug member 70 of second lead 64 to be introduced into second electrical connector 56 via opening 56A. In the example shown in FIG. 4, diameter 82 of second plug member 70 is less than or substantially equal to diameter 84 of first portion 75 of second electrical connector 56. Accordingly, when properly inserted, second portion 76 of second electrical connector 56 may receive second electrical contact portion 72 in a manner that electrically couples second lead 64 to second therapy module 48. When lead 64 is properly introduced into second electrical connector 56, electrical contacts 72A-72D of lead 64 may contact electrical contacts 76A-76D, respectively, of second portion 74 of second electrical connector 56. In some examples, electrical contacts 72A-72D and electrical contacts 76A-76D may have substantially similar surface areas, and when lead 64 is properly introduced into second electrical connector 56, electrical contacts 72A-72D and electrical contacts 76A-76D may substantially align such that a majority of the surface areas (e.g., greater than 75%) of each of the electrical contacts 72A-72D is in contact with a majority of the surface area of a respective electrical contact 76A-76D.

As previously indicated, electrical contacts 72A-72D of lead 64 may be electrically coupled to a respective stimulation or sensing electrode of lead 64 via conductors within a lead body of lead 64. Thus, aligning electrical contacts 72A-72D of lead 64 with electrical contacts 76A-76D of second electrical connector 56 may electrical connect the electrodes of lead 64 with second therapy module 48, which is electrically connected to electrical contacts 76A-76D.

As shown in FIGS. 3 and 4, first lead 62 is substantially incompatible with second electrical connector 56. For example, although first and second electrical contact portions conductors 68 and 72 may have similar dimensions, diameter 78 of first plug member 66 of first lead 62 is greater than diameter 84 of first portion 75 of second electrical connector 56, which helps prevent first electrical contact portion 68 from being introduced into second portion 77 of second electrical connector 56. In some examples, first lead 62 may be sized such that electrical contact portion 68 may be introduced into first portion 75 of second electrical connector 56. However, in such examples, electrical contacts 68A-68D of first lead 62 may not contact electrical contacts 76A-76D of second electrical connector 56 when electrical contact portion 68 is introduced into first portion 75 of second electrical connector 56. In this way, the incompatible configurations of second electrical connector 56 and first lead 62 help prevent electrical contacts 68A-68D of first lead 62 from electrically coupling to second therapy module 48 (FIG. 2), which is electrically coupled to electrical contacts 76 of second electrical connector 56. As a result, lead 62 may not deliver electrical stimulation signals generated by second therapy module 48 to heart 26 of patient 12.

Moreover, the difference in size between first plug member 66 and first portion 75 of second electrical connector 56 may indicate, e.g., to a clinician, that first lead 62 is not intended to be introduced into second electrical connector 56. This may further prevent inadvertent introduction of first lead 62 into second electrical connector 56. In addition, if lead 64 was introduced into first electrical connector 54, the loose fit between lead 64 and connector 54 would alert the clinician or other user that the leads 62, 64 may be reversed.

In the example shown in FIG. 4, another feature of lead connection assembly 40 that prevents the inadvertent delivery of electrical stimulation generated by second therapy module 48 (FIG. 2) to heart 26 of patient 12 is the configuration of electrical contacts 76 of second electrical connector 56 relative to the configuration of electrical contacts 68A-68D of first lead 62. As FIG. 4 illustrates, electrical contacts 68A-68D of lead 62 have a different relative spacing than electrical contacts 76A-76D of second electrical connector 56. Thus, even if the size of lead 62 permits electrical contact portion 68 of lead 62 to be introduced into second portion 77 of second electrical connector 56, at least some of electrical contacts 68A-68D may not align with or electrically connect with electrical contacts 76A-76D. In this way, an electrical connection between electrical contacts 68A-68D of lead 62 and electrical contacts 76A-76D may be minimized or even avoided, even if lead 62 is introduced into second electrical connector 56. The substantially incompatible electrical contact arrangement between lead 62 and second electrical connector 56 may be used instead of or in addition to the incompatible sizes.

In some examples, at least some of electrical contacts 68A-68D may at least partially contact electrical contacts 76A-76D, respectively, despite the different electrical contact arrangement (e.g., spacing). However, limited contact between at least some of electrical contacts 68A-68D, 76A-76D may still help minimize or even eliminate undesirable stimulation of heart 26 via electrical stimulation signals generated by second therapy module 48 (FIG. 2). For example, if one or two of electrical contacts 68A-68D fully contact a respective one of the electrical contacts 76A-76D, the intensity of stimulation delivered to heart 26 may be insufficient to generate undesirable physiological responses (e.g., an induced arrhythmia). As another examples, if one or more of electrical contacts 68A-68D partially contact one or more of electrical contacts 76A-76D, the intensity of stimulation delivered to heart 26 may be insufficient to generate undesirable physiological responses.

In some examples, each of the electrical contacts 68A-68D may be spaced from an adjacent electrical contact of lead 62 by a first distance of approximately 1 millimeters (mm) to about 6 mm, and each of electrical contacts 76A-76D may be spaced from an adjacent electrical contact of second electrical connector 56 by a second distance of approximately 1 mm to about 6 mm, where the first and second distances are different. Although FIG. 4 illustrates an example in which electrical contacts 76A-76D have a greater spacing relative to each other than electrical contacts 68A-68D, in other examples, electrical contacts 68A-68D may be spaced from each other by a greater distance than electrical contacts 76A-76D. In addition, electrical contacts 68A-68D, 76A-76D may not need to be spaced by an even distance. For example, electrical contacts 68A, 68B may be closer to each other than electrical contacts 68B, 68C.

In some examples, such as that shown in FIGS. 3 and 4, the size of second lead 64 may not necessarily be incompatible with first electrical connector 54, even if the size of first lead 62 is incompatible with second electrical connector 56. Diameter 80 of first portion 71 of first electrical connector 54 is greater than the diameter 82 of second plug member 70 of second lead 64, thereby permitting lead 64 to be introduced into first electrical connector 54. Thus, despite a difference in the dimensions of second lead 64 relative to first electrical connector 54, second plug 70 may be configured to be inserted into first electrical connector 54 in a manner that enables electrical contact portion 72 to be introduced into second portion 73 of first electrical connector 54. However, in some examples, the inadvertent delivery of at least one of pacing, cardioversion, or defibrillation therapy generated by first therapy module 46 (FIG. 2) to a nonmyocardial tissue site, e.g., an extravascular tissue site and/or site proximate a nerve, such as spinal cord 44, or a nonvascular cardiac tissue site may not cause the same nature and/or degree of undesirable side-effects as previously identified with respect to delivery of the second stimulation therapy to heart 26 of patient 12.

In the example shown in FIG. 4, electrical contacts 72A-72D of second lead 64 and electrical contacts 74A-74D of first electrical connector 54 have substantially different arrangements, such that even if electrical contact portion 72 of lead 64 is introduced into second portion 73 of first electrical connector 54, an electrical connection between first therapy module 46 (FIG. 2) and electrodes of lead 64 may not established, or at least minimized. In the example shown in FIG. 4, electrical contacts 72A-72D of second lead 64 are spaced from each other by a greater distance than the distance with which electrical contacts 74A-74D of electrical connector 54 are spaced from each other. In this way, second lead 64 and first electrical connector 54 may be incompatible.

Figure 5:
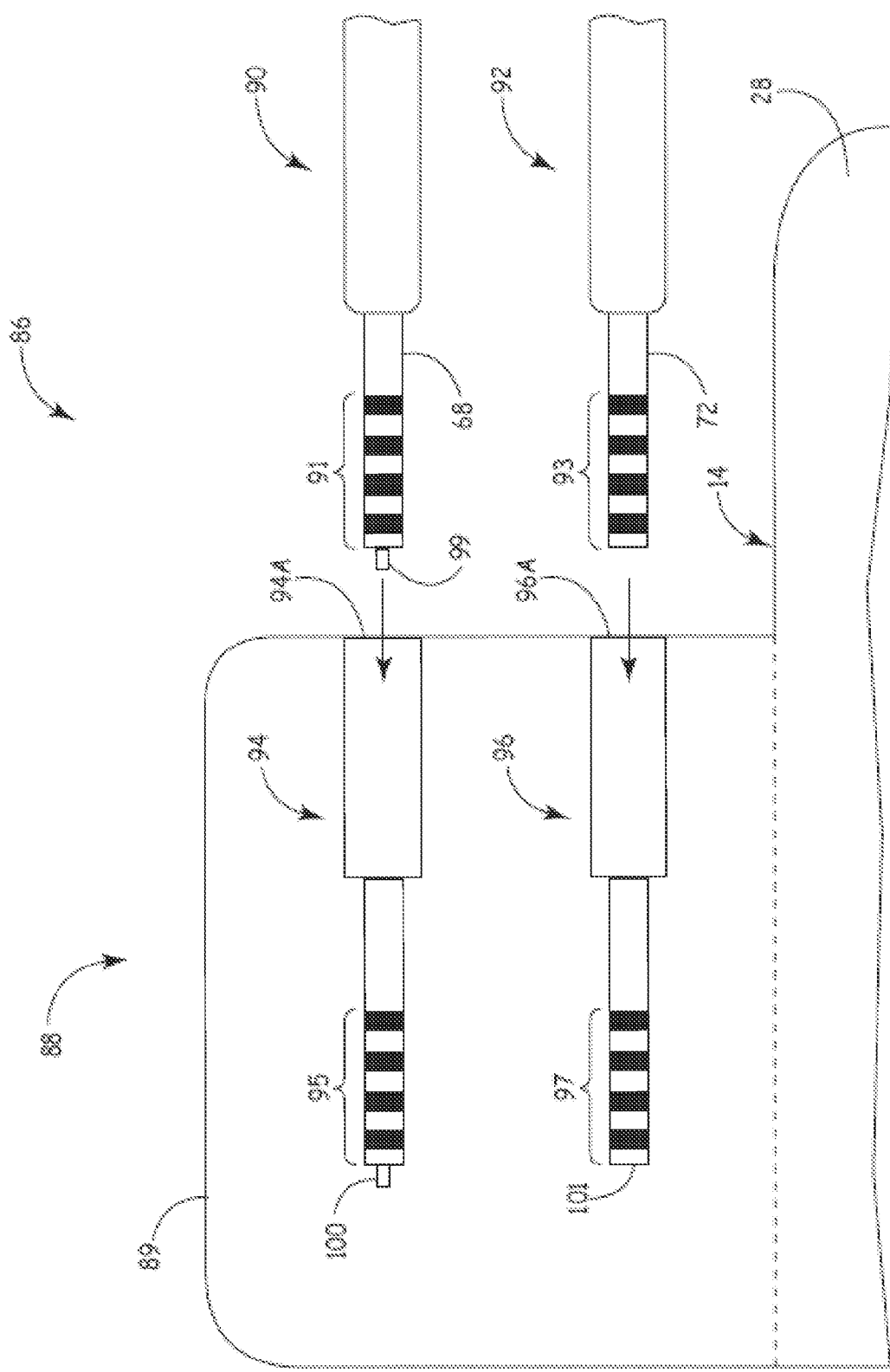
FIG. 5 is a conceptual diagram illustrating a cross-sectional view of a portion of another example therapy system that includes an electrical connector that is substantially physically incompatible with a lead.

FIG. 5 is a conceptual diagram illustrating a cross-sectional view another example therapy system 86, which includes IMD 14, lead connection assembly 88, first lead 90, and second lead 92. Lead connection assembly 88 may be connected to IMD 14, e.g., as described with respect to lead connection assembly 40 of FIG. 1.

Lead connection assembly 88 includes first electrical connector 94 and second electrical connector 96, which have substantially similar sized openings 94A, 96A defined by housing 89 of lead connection assembly 88. First electrical connector 94 comprises a set of electrical contacts 95 that are electrically connected to first therapy module 46 (FIG. 2). First lead 90 may be introduced into first electrical connector 94 such that electrical contacts 91 of lead 90 substantially align with and contact electrical contacts 95 of electrical connector 94 in order to establish an electrical connection between first therapy module 46 and one or more stimulation and/or sensing electrodes of lead 90, which are electrically coupled to a respective one of the electrical contacts 91. In this way, first therapy module 46 may deliver at least one of pacing, cardioversion or defibrillation therapy to heart 26 (FIG. 1) of patient 12 via electrodes of first lead 90.

Second electrical connector 96 comprises a set of electrical contacts 97 that are electrically connected to second therapy module 48 (FIG. 2) of IMD 14. Second lead 92 may be introduced into second electrical connector 96 such that electrical contacts 93 of lead 92 may substantially align with and contact electrical contacts 97 of second electrical connector 96 in order to establish an electrical connection between second therapy module 48 and one or more stimulation and/or sensing electrodes of lead 92, which are electrically coupled to a respective one of the electrical contacts 93. In this way, second therapy module 48 may deliver stimulation therapy to a tissue site within patient 12 via electrodes of second lead 92.

The relative physical dimensions of the portions of first and second leads 90, 92, respectively, which may be received by first and second electrical connectors 94, 96, respectively, are substantially similar. Accordingly, the physical dimensions of first lead 90 do not prevent first lead 90 from being inserted into opening 96A of second lead connector 96 and, likewise, the physical dimensions of second lead 92 do not prevent second lead 92 from being inserted into opening 94A of first electrical connector 94.

In addition, in the example shown in FIG. 5, electrical contacts 91 of first lead 90 have a substantially similar arrangement as electrical contacts 97 of second electrical connector 96. Thus, lead 90 and second electrical connector 96 are configured such that electrical contacts 91 of first lead 90 may substantially align with and contact electrical contacts 97, thereby establishing an electrical connection between second therapy module 48 (FIG. 2) and lead 90. As described above, this may be undesirable because the delivery of electrical stimulation signals generated by second therapy module 48 may cause undesirable physiological responses by heart 26.

In order to help prevent first lead 90 from being introduced into second electrical connector 96, e.g., to prevent first lead 90 from delivering electrical stimulation signals generated by second therapy module 48 to heart 26, first lead 90 may include center pin 99. Center pin 99 may be configured to slide into hollow center bore 100 defined by first electrical connector 94 of lead connection assembly 88. Center pin 99 of lead 90 configures lead 90 such that it is substantially physically incompatible with second electrical connector 96. As shown in FIG. 5, when first lead 90 is introduced into second electrical connector 96, center pin 99 of lead 90 may contact wall 101, which prohibits lead 90 from being fully introduced into second electrical connector 96. Moreover, center pin 99 may interfere with the ability of electrical contacts 91 of first lead 90 to align with electrical contacts 97 of second electrical connector 96, thereby preventing the electrodes of first lead 90 from electrically connecting to second therapy module 48 (FIG. 2). Center pin 99 may also prevent alignment of one or more visible alignment markers associated with lead 90 and/or second electrical connector 96, which may indicate improper connection of lead 90 with second electrical connector 96.

In some examples, center pin 99 is an electrically conductive component of lead 90, and bore 100 includes an electrical contact. In such an example, lead 90 is only configured to deliver stimulation to patient 12 if center pin 99 makes electrical contact with lead 90. Processor 45 of IMD 14 (FIG. 2) may determine whether center pin 99 is in electrical contact with lead 90 prior to controlling therapy module 46 to deliver electrical stimulation to electrodes of lead 90. For example, processor 45 may determine an impedance of an electrical path including the center pin 99 and compare the impedance to a stored threshold value or a range of stored threshold values to determine whether the impedance indicates center pin 99 is in electrical contact with lead 90.

In some examples, second electrical connector 96 may be configured manner that does not allow delivery of electrical stimulation to patient via lead 90 unless all electrical contacts 91 of first lead 90 are in contact with electrical contacts 97 of second electrical connector 96. For example, although the spacing between adjacent electrical contacts 91 may be consistent with the spacing between adjacent electrical contacts 97 such that less than all of the individual contacts, e.g., three of the four contacts shown) may be brought fully into contact with one another when lead 90 is partially inserted in electrical connector 96, second electrical connector 96 may be configured in a manner that does not allow delivery of electrical stimulation via lead 90 unless each of the four electrical contacts 97 are in contact with the corresponding electrical contacts 91 of first lead 90. In this manner, even though electrical contacts 91 of first lead 90 may have substantially the same configuration of electrical contacts 97 of second lead connector 96, first lead 90 may still be prevented from electrically coupling to second therapy module 48 (FIG. 2) via second electrical connection 96 even though more than one of the electrical contacts 91 of lead 90 are in contact with electrical contacts 97 of second electrical connector 96, so long as each of the individual electrical contacts 91 of lead 90 are not in contact with a respective one of the electrical contacts 97.

In the example shown in FIG. 5, the different geometrical configuration of first lead 90 relative to second electrical connector 96 prevents first lead 90 from being electrically coupled to second therapy module 48, even when first lead 90 is inserted into second electrical connector 96. Accordingly, first lead 90 may be considered incompatible with second lead connector 96.

Although not shown in FIG. 5, second lead 92 may also have a geometrical configuration that prevents electrical contacts 93 of second lead 92 from electrically connecting to electrical contacts 95 of first electrical connector 94. For example, second lead 92 may have a center pin (not shown) similar to center pin 99 of first lead 90, where the center pin of second lead 92 may have a different cross-sectional shape than center pin 99. The cross-sectional shape of center pin 99 may be configured such that it may not be introduced into a bore defined by second electrical connector 96. The cross-sectional shape referred to may be a shape of the cross-section of the center pin taken in a direction substantially orthogonal to a center axis of the respective lead 90, 92. As an example, center pin 99 of first lead 90 may have a circular cross-sectional shape, while the center pin of second lead 92 may have an oblong or a rectangular cross-sectional shape.

Figure 6:
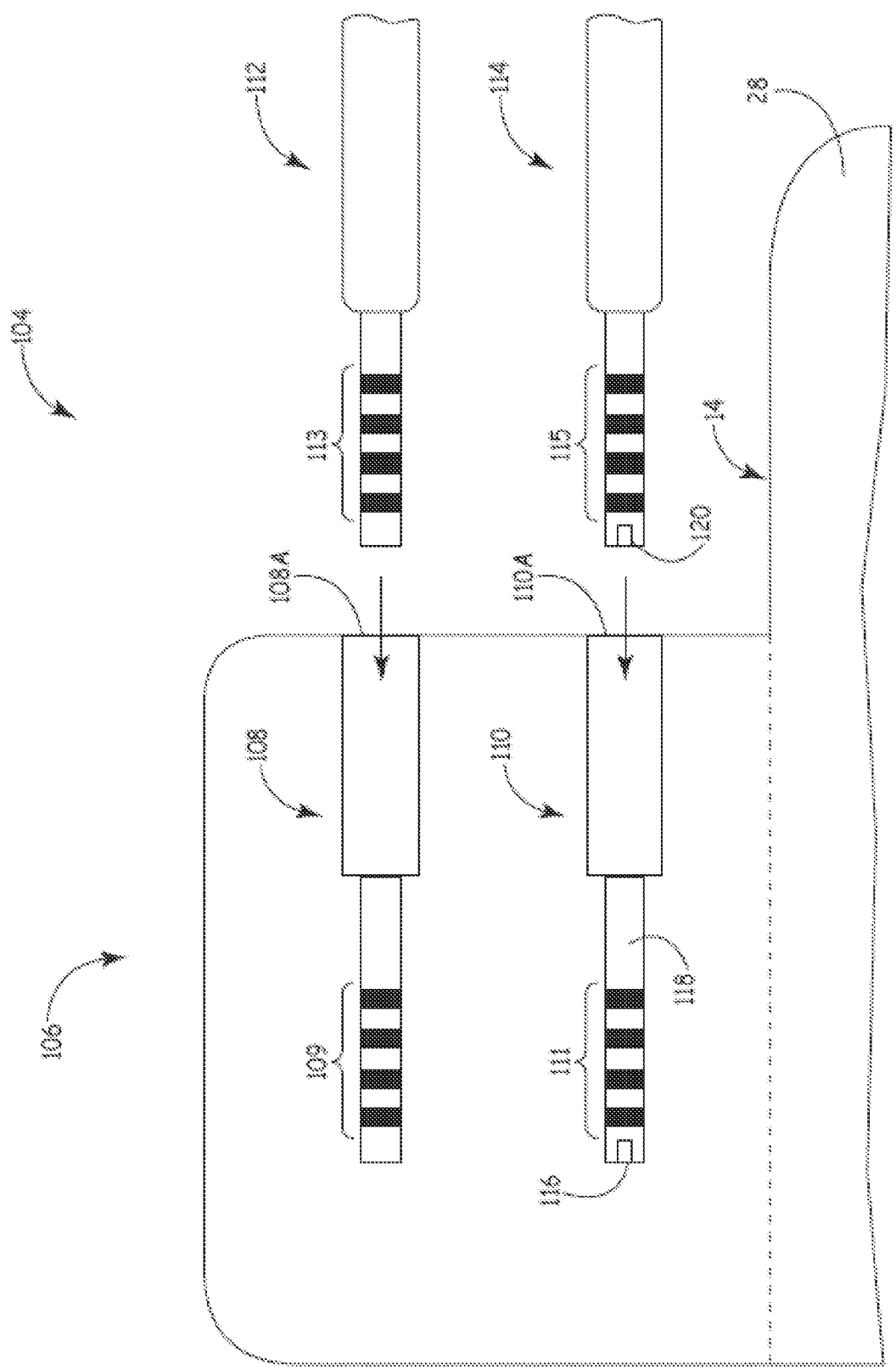
FIG. 6 is a conceptual diagram illustrating a cross-sectional view of a portion of another example therapy system that includes an electrical connector that is substantially physically incompatible with a lead.

FIG. 6 is a conceptual diagram illustrating a cross-sectional view of a portion of another example therapy system 104. Therapy system 104 comprises IMD 14, which includes lead connection assembly 106 comprising first electrical connector 108 including electrical contacts 109 that are electrically coupled to first therapy module 46 (FIG. 2) and second electrical connector 110 including electrical contacts 111 that are electrically coupled to second therapy module 48 (FIG. 2). Therapy system 104 further comprises first lead 112 including electrical contacts 113 and second lead 114 including electrical contacts 115.

First lead 112 may be introduced into first electrical connector 108 such that electrical contacts 113 of lead 112 substantially align with and contact electrical contacts 109 of electrical connector 108 in order to establish an electrical connection between first therapy module 46 and one or more stimulation and/or sensing electrodes of lead 112, which are electrically coupled to a respective one of the electrical contacts 113. In this way, first therapy module 46 may deliver at least one of pacing, cardioversion or defibrillation therapy to heart 26 of patient 12 via electrodes of first lead 112.

Second lead 114 may be introduced into second electrical connector 110 such that electrical contacts 115 of lead 114 substantially align with and contact electrical contacts 111 of electrical connector 110 in order to establish an electrical connection between second therapy module 48 (FIG. 2) and one or more stimulation and/or sensing electrodes of lead 114, which are electrically coupled to a respective one of the electrical contacts 115. In this way, second therapy module 48 may deliver electrical stimulation therapy to a nonmyocardial tissue site, e.g., a tissue site proximate a nerve and/or an extravascular tissue site, or a nonvascular cardiac tissue site within patient 12 via electrodes of second lead 114.

As with therapy system 86 of FIG. 5, the relative physical dimensions of the portions of first and second leads 112, 114 that may be received by first and second electrical connectors 108, 110, respectively, are substantially similar. Accordingly, the physical dimensions of first lead 112 may not help prevent first lead 112 from being introduced into second lead connector 110. In addition, in the example shown in FIG. 6, first and second leads 112, 114 have substantially similar electrical contact 113, 115 arrangements (e.g., spacing between the electrical contacts) and first and second electrical connectors 108, 110 have substantially similar electrical contact 109, 111 arrangements. In this way, second electrical connector 110 may be substantially electrically compatible with first lead 112.

In order to prevent first lead 112 from delivering electrical stimulation signals generated by second therapy module 48 to heart 26, second electrical connector 110 may include pin 116. Pin 116 protrudes into cavity 118 of second electrical connector 110. Second lead 114 may define bore 120 (e.g., an opening) that is configured to receive pin 116, such that when second lead 114 is introduced into opening 110A of second electrical connector 110, pin 116 may be received in bore 120. In this way, electrical contacts 111 of second electrical connector 110 substantially align with and contact a respective one of the electrical contacts 115 of second lead 114. In some examples, electrical contacts 111 may substantially fully contact a respective one of the electrical contacts 115 of second lead 114.

In therapy system 104, first lead 112 that may be positioned to deliver stimulation to heart 26, however, does not include a bore. Thus, if first lead 112 is introduced into second electrical connector 110, pin 116 may interfere with the ability of first lead 112 to be fully introduced into cavity 118 of second electrical connector 110. This may help prevent the electrical contacts 113 of first lead 112 from substantially aligning with electrical contacts 111 of second electrical connector 110. In this way, second electrical connector 110 is configured to be substantially physically incompatible with first lead 112. The physical incompatibility between second electrical connector 110 and first lead 112 may help limit or prevent first lead 112 from delivering electrical stimulation generated by second therapy module 48 to heart 26 of patient 12.

In the example shown in FIG. 6, the different geometrical configuration of first lead 112 relative to second electrical connector 110 prevents first lead 112 from being electrically coupled to second therapy module 48, even when first lead 112 is introduced into second electrical connector 110.

In some examples of therapy system 104, pin 116 of second electrical connector 110 may be conductive, and bore 120 of lead 114 may include an electrical contact that is configured to electrically contact a conductive pin 116. Processor 45 of IMD 14 (FIG. 2) may be configured to control second therapy module 48 (FIG. 2) to deliver electrical stimulation via a connected lead only if conductive pin 116 electrically connects to the electrical contact within bore 120. In this way, processor 45 may verify that the proper lead 114 is introduced into second electrical connector 110. Processor 45 of IMD 14 (FIG. 2) may determine whether pin 116 is in electrical contact with lead 90 prior to controlling therapy module 46 to deliver electrical stimulation to electrodes of lead 114. For example, processor 45 may determine an impedance of an electrical path including the center pin 116 and compare the impedance to a stored threshold value or a range of stored threshold values to determine whether the impedance indicates center pin 116 is in electrical contact with lead 114.

Although leads including four electrical contacts are shown in FIGS. 4-6, in other examples, a lead may include any suitable number of electrical contacts. In some examples, the number of electrical contacts located at a proximal portion of the lead may correspond to the number of stimulation and/or sensing electrodes at a distal portion of the lead. In addition, the electrical connectors described herein may include any suitable number of electrical contacts, which may correspond to the number of electrical contacts on a proximal portion of a lead that is introduced into the electrical connector.

Figure 7:
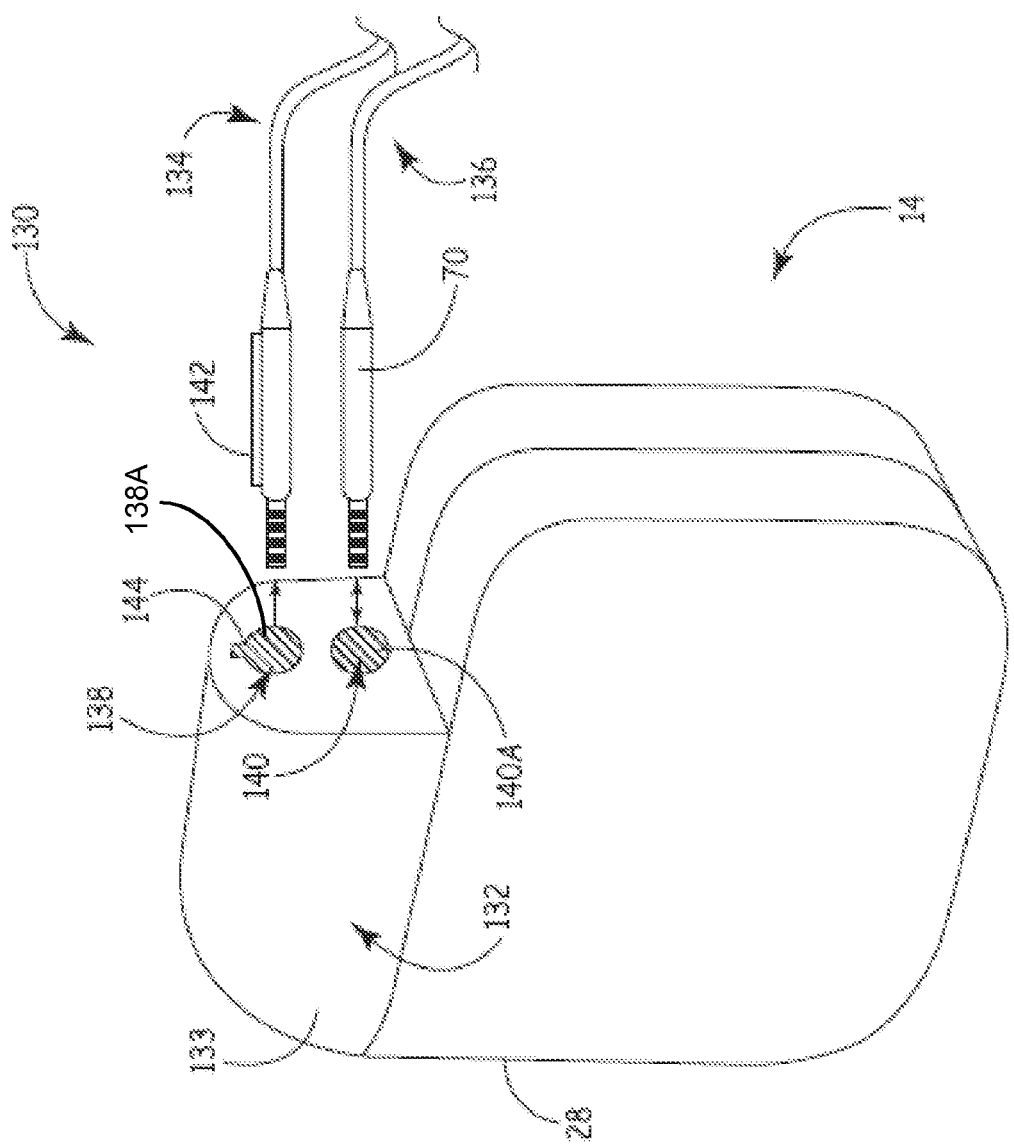
FIG. 7 is a conceptual diagram illustrating a perspective view of an example therapy system that includes an electrical connector that is substantially physically incompatible with a lead.

FIG. 7 is a conceptual diagram illustrating a perspective view of example therapy system 130, which includes IMD 14, lead connection assembly 132, first lead 134, and second lead 136. IMD 14 is described above with respect to FIGS. 1 and 2. Lead connection assembly 132 includes first electrical connector 138 that includes electrical contacts that are electrically coupled to first therapy module 46 (FIG. 2) and second electrical connector 140 that includes electrical contacts that are electrically coupled to second therapy module 48 (FIG. 2). First lead 134 may be introduced into first electrical connector 138 to electrically connect electrodes carried by first lead 134 to first therapy module 46. In addition, second lead 136 may be introduced into second electrical connector 140 in order to electrically connect electrodes carried by second lead 136 to second therapy module 48.

In the example shown in FIG. 7, second electrical connector 140 is configured to be substantially physically incompatible with first lead 134 in order to discourage a clinician from introducing first lead 134 into second electrical connector 140. While openings 138A, 140A of first and second electrical connectors 138, 140, respectively, are substantially similar in size, openings 138A, 140A may have different geometrical configurations. First lead 134 defines flange 142 and first electrical connector 138 defines a channel 144 that is configured to receive flange 142. Second electrical connector 140, on the other hand, does not define a channel that is configured to receive flange 142. As a result, first lead 134 may not be substantially fully introduced into second electrical connector 140. For example, flange 142 may interfere with the ability of lead 134 to be introduced into opening 140A of second electrical connector 140. In this way, first lead 134 may be considered to be physically incompatible with second electrical connector 140.

The physical incompatibility between second electrical connector 140 and first lead 134 may help prevent the electrodes of first lead 134 from being fully electrically connected to electrical contacts within second electrical connector 140. In some cases, some of the electrical contacts on a proximal portion of first lead 134 may contact electrical contacts of second electrical connector 140. However, this electrical connection between first lead 134 and second electrical connector 140 may be insufficient to deliver undesirable electrical stimulation to heart 26 from second therapy module 48.

In other examples, other configurations of flange 142 and channel 144 are contemplated, such as different sizes and different shapes. Flange 142 of lead 134 may comprise any suitable protrusion that extends around any suitable portion of outer perimeter of lead 134. In some examples, lead 134 may include a plurality of flange 142 with connector 138 including a plurality of channels 144 in a configuration that corresponds to the plurality of flanges of lead 134. Although in FIG. 7, only first electrical connector 138 defines channel 144 and only first lead 134 includes flange 142, in some examples, both first and second electrical connectors 138, 140, respectively, may define channels, and both leads 134, 136 may include protrusions that are configured to be received in the channels of first and second electrical connectors 138, 140. However, first and second electrical connectors 138, 140, respectively, may define different types of channels, such that second electrical connector 140 is substantially physically incompatible with the flange of first lead 134.

Alternatively or additionally, although not indicated in FIG. 7, one or more of electrical connectors 138 and 140 may possess particular magnetic properties such that second electrical connector 140 is configured to be substantially physically incompatible with first lead 134 in order to discourage a clinician from introducing first lead 134 into second electrical connector 140. For example, first electrical connector 138 may exhibit a first magnetic polarity relative opening 138A and second electrical connector 140 may exhibit a second magnetic polarity relative opening 149A that is substantially opposite of that the first magnetic polarity. In such a case, plug portion of first lead 134 may be configured to be magnetically compatible with the first magnetic polarity of first electrical connector 138 and, thus, magnetically incompatible with the second magnetic polarity of second electrical connector 140. In this manner, not only does the magnetic property of second electrical connector 140 repel attempts to introduce plug portion of first lead 134 into second electrical connector 140, the magnetic property of first electrical connector 138 may encourage connection with lead 134 and act to secure the plug portion of lead 134 within first electrical connector 138 via magnetic forces.

Similarly, in some examples, plug portion 70 of second lead 136 is configured to be magnetically compatible with the second magnetic polarity of second electrical connector 140 and, thus, magnetically incompatible with the first magnetic polarity of first electrical connector 138. In such a case, not only does the magnetic property of first electrical connector 138 repel attempts to introduce plug portion 70 of second lead 136 into first electrical connector 138, the magnetic property of second electrical connector 140 may encourage connection with lead 136 and act to secure plug 70 of lead 136 within first electrical connector 140 via magnetic forces.

Lead connection assemblies 40 (FIGS. 2-4), 88 (FIG. 5), 106 (FIG. 6), 132 (FIG. 7) described herein are configured to receive two leads. As previously indicated, in other examples, lead connection assemblies in accordance with the examples described herein may be configured to receive more than two leads, e.g., via a respective electrical connector. In examples in which a lead connection module includes more than two electrical connectors, the electrical connectors may be configured to have different geometrical configurations, electrical contact configurations, different sized openings, and/or different visual identifiers (e.g., color bands or alphanumeric identifiers). In this way, electrical connector may be configured to receive only a certain type of lead. In other examples, two of the electrical connectors may share a geometrical configurations, electrical contact configurations, and/or opening size. For example, electrical connectors used to electrically couple a respective one of the leads 18, 20, 22 (FIG. 1) to first therapy module 46 (FIG. 1) may share similar features, such that leads 18, 20, 22 may be introduced into any of the electrical connectors. In other examples, the electrical connectors of the lead connection assembly may be configured to receive a specific lead 18, 20, 22.

Figure 8:
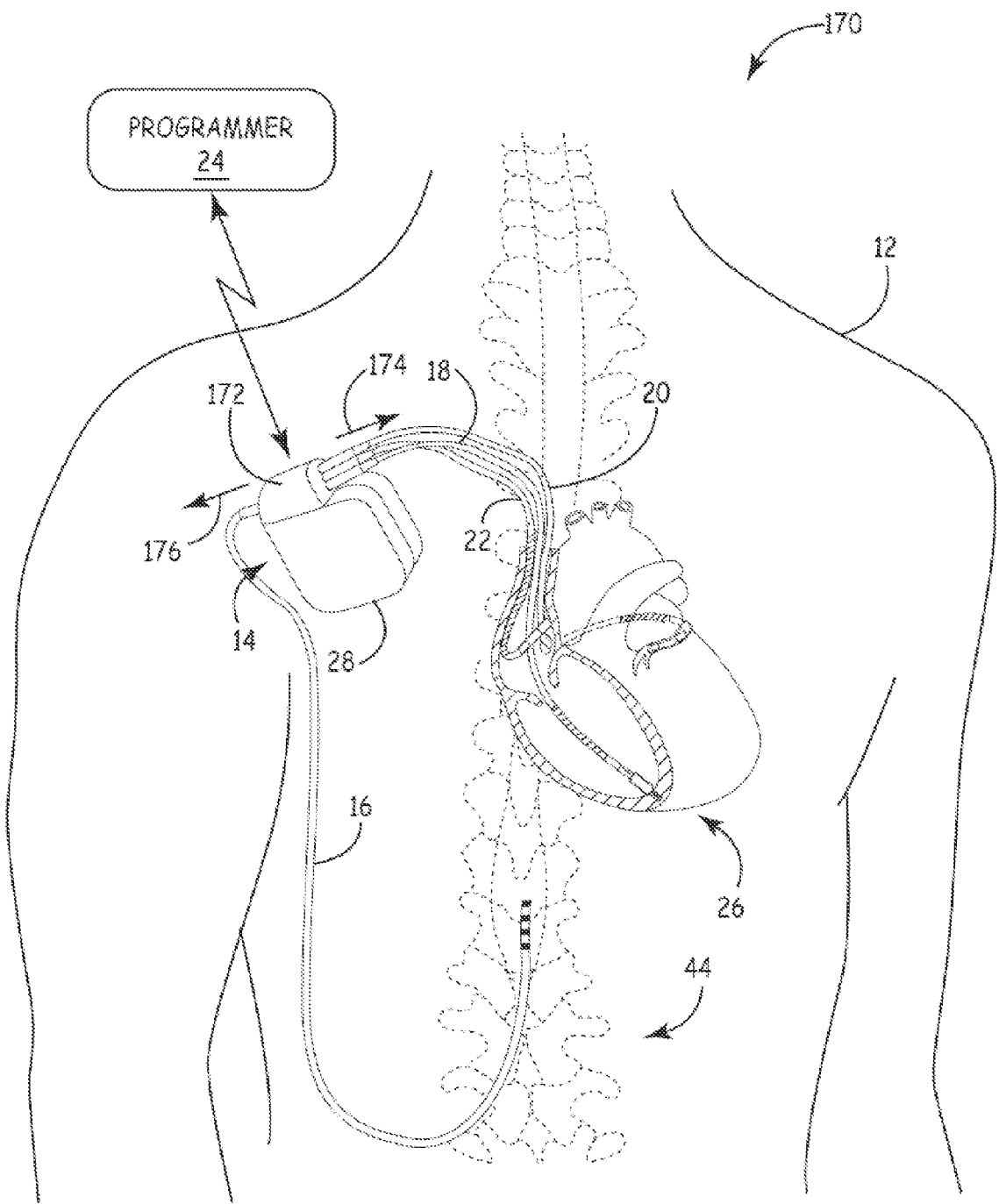
FIG. 8 is a conceptual diagram illustrating an example therapy system that includes an IMD including a lead connection assembly that includes electrical connectors defining openings for receiving leads that extend in substantially opposite directions.

FIG. 8 is a conceptual diagram illustrating an example therapy system 170 that delivers at least one of pacing, cardioversion or defibrillation therapy to heart 26, and delivers electrical stimulation to a nonmyocardial tissue site, e.g., an extravascular tissue site and/or tissue site proximate a nerve of patient 12 or a nonvascular tissue site within patient 12. System 170 may be substantially the same or similar to system 10 of FIG. 1. However, IMD 14 includes lead connection assembly 172 that is configured to accommodate different lead approaches, e.g., different angles with which leads 16, 18, 20, 22 may be mechanically coupled to lead connection assembly 172.

Lead connection assembly 172 is configured such that leads 18, 20, 22 may extend from lead connection assembly 172 in a first direction, which is represented by arrow 174, and lead 16 may extend from lead connection assembly 172 in a second direction, which is represented by arrow 176. In particular, first direction 174 corresponds to a direction in which a proximal end of each of the leads 18, 20, 22 may be introduced into lead connection assembly 172, and second direction 176 corresponds to a direction in which a proximal end of lead 16 may be introduced in lead connection assembly 172. First direction 174 is substantially different from that of second direction 176. In the example shown in FIG. 8, first and second directions 174, 176, respectively, may be substantially opposite to each other. Lead connection assembly 172 may define openings that face in direction 174, and an opening that faces in direction 176, whereby leads 18, 20, 22 may be introduced into the openings that face in direction 174 and a lead 16 may be introduced into the openings that face in direction 176.

In some examples, leads 18, 20, 22 extending from lead connection assembly 172 in first direction 174 may accommodate the implantation of electrodes of leads 18, 20, 22 within heart 26. Similarly, lead 16 extending from lead connection assembly 172 in second direction 176 may accommodate the implantation of electrodes of lead 16 proximate the respective target stimulation site for the delivery of electrical stimulation generated by second therapy module 48 (FIG. 2). For example, first direction 174 may correspond to the relative direction of the path that leads 18, 20, 22 may follow from IMD 14 to heart 26 when implanted in patient 12, and second direction 176 may correspond to the relative direction of the path that lead 16 may follow from lead connection assembly 172 to spinal cord 44 when implanted in patient 12.

In some examples, lead connection assembly 172 that accommodates the extension of leads from housing 28 in different directions, e.g., via openings that face in different directions, for accommodating the different target stimulation sites of therapy system 10 may minimize the length of a lead implanted in patient 12 to reach from IMD 14 the target stimulation location, such as, e.g., spinal cord 44 and/or heart 26. This may help decrease the overall intensity of stimulation required to stimulation tissue by decreasing the impedance of the electrical path between the therapy modules 46, 48 of IMD 14 and the target stimulation site. Decreasing the intensity of stimulation required to stimulate tissue may help conserve power source 50 (FIG. 2) of IMD 14, which may extend the useful life of IMD 14. An intensity of stimulation may be a function of, for example, a current or voltage amplitude of stimulation signal, the frequency of the stimulation signal, the shape of the stimulation signal, the duty cycle of the stimulation signal, or the electrode combination used to deliver the stimulation signal.

Lead connection assembly 172 that accommodates the extension of leads from housing 28 in different directions, e.g., via openings that face in different directions, for accommodating the different target stimulation sites of therapy system 10 may also help maintain the integrity of leads 16, 18, 20, 22 by decreasing the stresses imposed on leads 16, 18, 20, 22 attributable to traversing a path including one or more sharp turns. That is, lead connection assembly 172 may help decrease the number of sharp turns or other awkward lead 16, 18, 20 or 22 configurations in a path from IMD 14 to a target tissue site within patient 12. This may help decrease the stresses on leads 16, 18, 20, 22, which may help increase the integrity of conductors within the respective lead and/or the insulation of the respective lead that separates the electrical conductors from each other and/or from tissue of patient 12. This may also simplify the lead connection process and also reduce the length and/or amount of leads located within the pocket related to the implant. For example, the extension of leads from different direction may assist a physician in identifying the proper connector corresponding to particular type of lead, thereby encouraging connection of a lead into the particular electrical connector and discouraging connecting the lead into an improper connector. Such a configuration may decrease the likelihood of inadvertent connection of a lead to the improper electrical connector, and increase the efficiency of the device implantation procedure.

Figure 9:
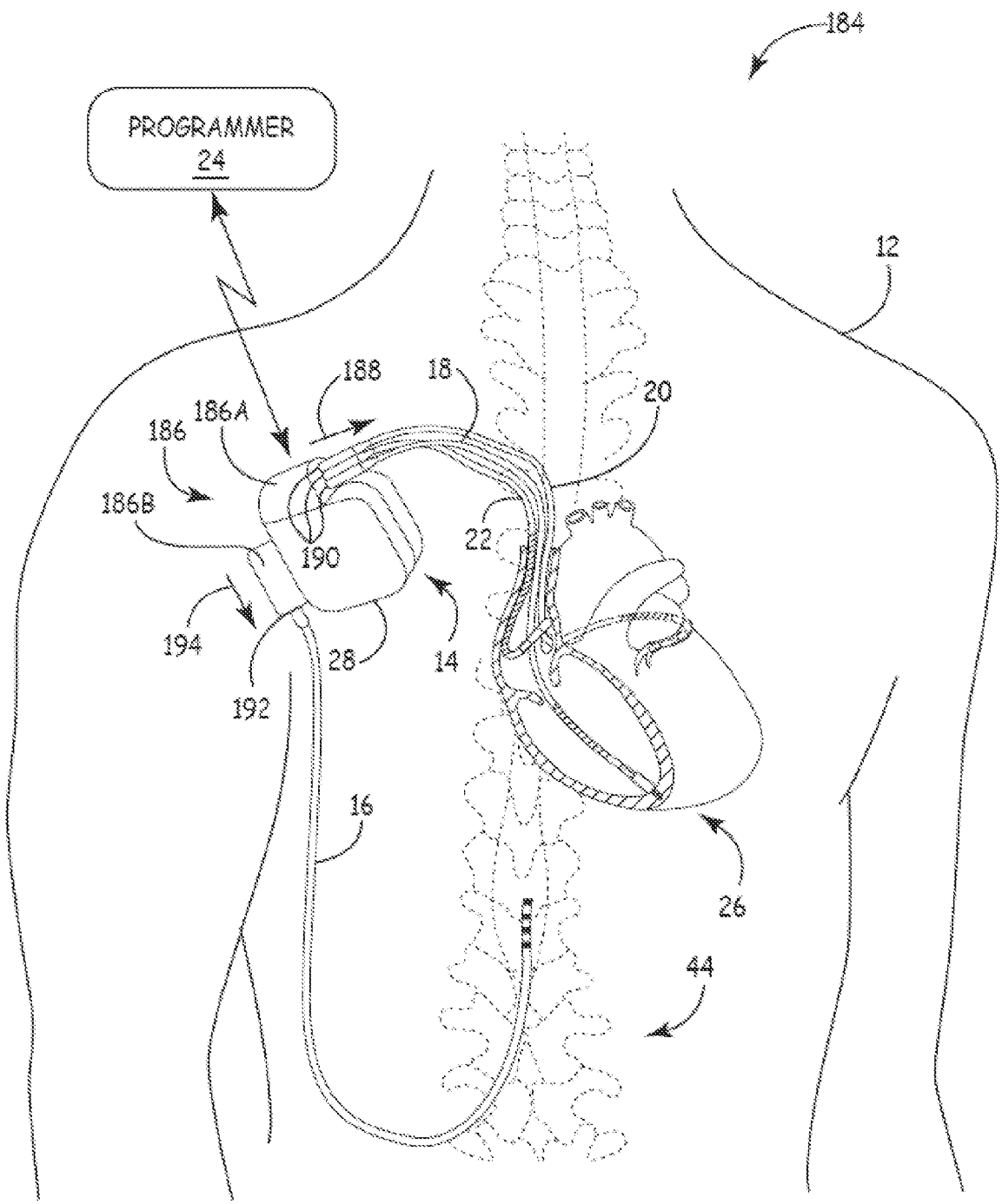
FIG. 9 is conceptual diagram illustrating an example therapy system that includes an IMD including a lead connection assembly that includes electrical connectors defining openings for receiving leads that extend in substantially different directions.

FIG. 9 is conceptual diagram illustrating another example therapy system 184 that may be used to deliver at least one of pacing, cardioversion or defibrillation therapy to heart 26, and deliver electrical stimulation to a nonmyocardial tissue site, e.g., an extravascular tissue site and/or tissue site proximate a nerve of patient 12. System 184 may be substantially similar to system 170 of FIG. 9. However, IMD 14 is connected to lead connection assembly 186 rather than lead connection assembly 172. Lead connection assembly 186 includes first electrical connector 186A and second electrical 186B. First electrical connector 186A connects electrodes of leads 18, 20, 22 to IMD 14 to first therapy module 46 (FIG. 2) of IMD 14. Second electrical connector 186B connects electrodes of lead 16 to second therapy module 48 (FIG. 2) of IMD 14.

As shown in FIG. 9, first electrical connector 186A is configured such that leads 18, 20, 22 extend from housing 28 of IMD 14 in a first direction 188. For example, first electrical connector 186A may define openings 190 through which leads 18, 20, 22 may be introduced into lead connection assembly 186. Second connection assembly 186B is configured such that lead 16 extends from housing of IMD 14 in a second direction 194 that is different than first direction 188. For example, second electrical connector 186B may define opening 192 through which lead 16 may be introduced into lead connection assembly 186. Opening 192 may face a different direction than openings 190 of first electrical connector 186A.

In the example of FIG. 9, first direction 188 may be a direction of a physical path between IMD 14 and a target stimulation site for the pacing, cardioversion and/or defibrillation signals delivered via electrodes of leads 18, 20, 22. Second direction 194 may correspond to a direction of a physical path between IMD 14 and a target stimulation site for electrical stimulation generated by second therapy module 48 (FIG. 2) via electrodes of lead 16. In some examples, directions 188, 194 may be substantially orthogonal to each other, although other relative directions with which leads 18, 20, 22 and lead 16 may extend from housing 28 of IMD 14 are also contemplated.

As discussed with respect to FIG. 8, lead connection assembly 186 that permits leads to extend therefrom in different directions may help increase the ease with which therapy system 184 may be implanted within patient 12, despite the fact that leads 18, 20, 22 and lead 16 may deliver stimulation to substantially different tissue sites within patient 12. In addition, lead connection assembly 186 may help minimize the length of one or more of the leads 16, 18, 20, 22 by enabling a clinician to implant therapy system 10 such that at least one of the leads 16, 18, 20, 22 extends from IMD 14 to a target tissue site via a more direct route. Further, just as with lead connection assembly 172 (FIG. 8), lead connection assembly 186 may help decrease the stresses imposed on at least one of the leads 16, 18, 20, 22 by decreasing the turns that the lead may take in the traversal from IMD 14 to a target tissue site.

Figure 10:
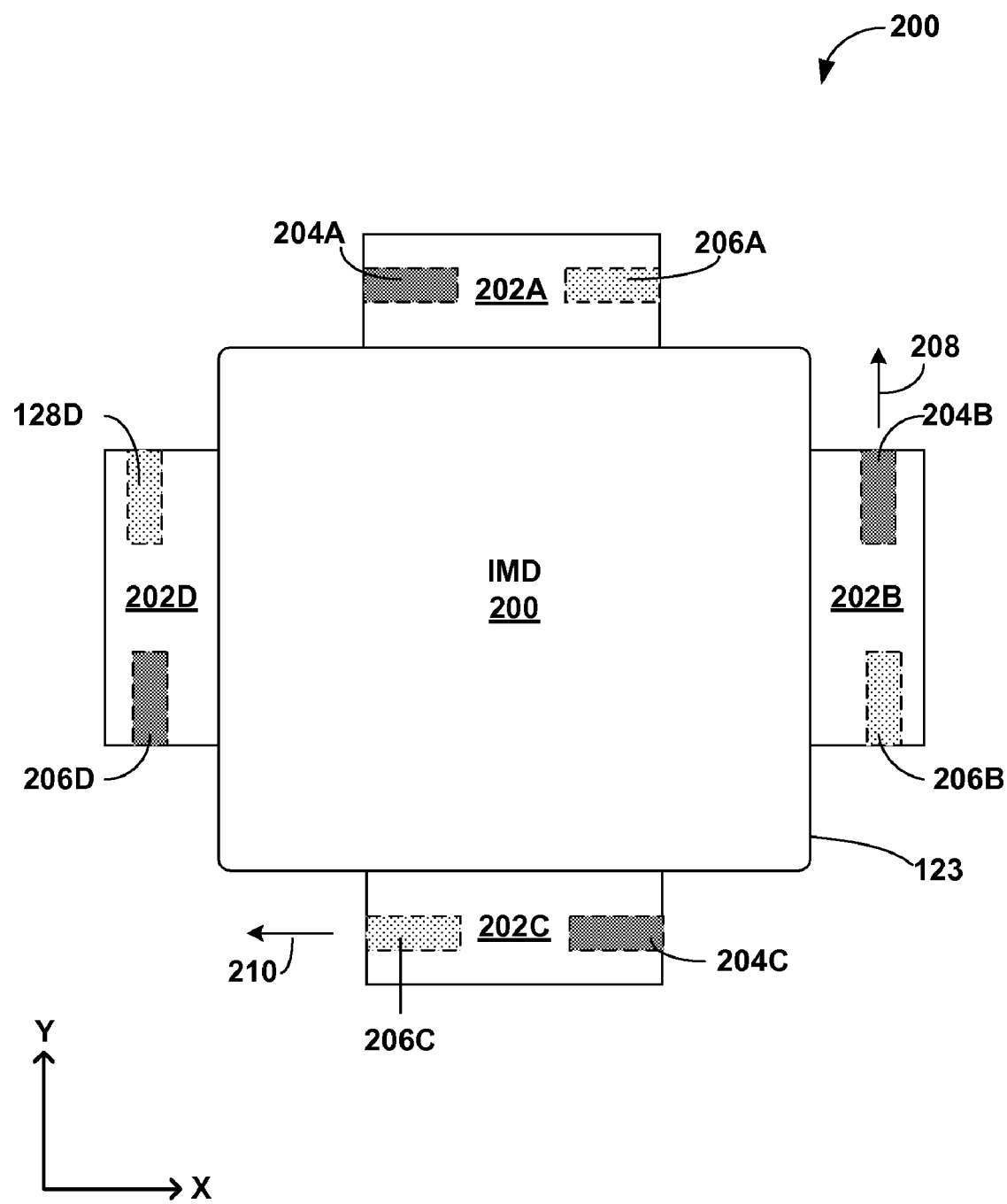
FIG. 10 is a conceptual diagram illustrating an example IMD comprising a lead connection assembly with a plurality of electrical connectors.

FIG. 10 is a conceptual diagram illustrating example IMD 200 and electrical connection assemblies 202A, 202B, 202C, 202D (collectively "electrical connection assemblies 202"). Each lead connection assembly 202A-202D includes a first electrical connector 204A-204D, respectively, and a second electrical connector 206A-206D, respectively. First electrical connectors 204A-204D and second electrical connectors 206A-206D may be receptacle type electrical connectors configured to receive a proximate portion of one or more implantable leads (not shown). For example, each of the first electrical connectors 204A-204D may be substantially similar to first electrical connector 54 of lead connection assembly 40 (FIG. 2) or first electrical connector 94 of lead connection assembly 88 (FIG. 5), and each of the second electrical connectors 206A-206D may be substantially similar to second electrical connector 56 of lead connection assembly 40 (FIG. 2) or second electrical connector 96 of lead connection assembly 88 (FIG. 5).

In some examples, each first electrical connector 204A-206D may be configured to electrically couple one or more leads to a first therapy module, such as, e.g., first therapy module 46, to deliver a first type of electrical stimulation to patient 12 (e.g., at least one of a pacing, cardioversion or defibrillation therapy). In addition, in some examples, each second electrical connector 206A-206D may be configured to electrically couple one or more leads to a second therapy module, such as, e.g., first therapy module 48, to deliver a second type of electrical stimulation to patient 12.

Electrical connection assemblies 202 may each mechanically couple to leads, such that the leads extend in different directions. Electrical connection assemblies 202A-202D may each define openings that face in substantially opposite directions. In the example shown in FIG. 10, electrical connection assemblies 202A, 202C each define openings that face in substantially positive direction along an x-axis (orthogonal x-y axes are shown in FIG. 10) and a substantially negative direction along the x-axis. In the example shown in FIG. 10, electrical connection assemblies 202B, 202D each define openings that face in substantially positive direction along a y-axis and a substantially negative direction along the y-axis.

One or more leads may be coupled to any one or more electrical connection assemblies in order to deliver therapy from IMD 200 to patient 12. Moreover, both electrical connectors 204A-204D, 206A-206D of each electrical connection assembly 202 need not be used at the same time. For example, a first lead may be introduced into electrical connector 204B of lead connection assembly 202B to electrically couple the first lead to the first therapy module of IMD 200, such that the first lead extends from housing 123 of IMD 200 in a first direction 208, e.g., approximately the positive y-axis direction. At the same time, a second lead may be introduced into electrical connector 206C of lead connection assembly 202C to electrically couple the second lead to the second therapy module of IMD 200, such that the second lead extends from housing 123 in a second direction 210, e.g., approximately the negative x-axis direction.

IMD 200 including electrical connection assemblies 202 that define lead-receiving openings that face in different directions may support a greater number of IMD 200 implant sites within patient 12 and/or therapy delivery to a greater number of target stimulation sites within patient 12. During implantation of a therapy system including IMD 200 and one or more leads in patient 12, a clinician may adapt the therapy system to different implantation sites within patient 12, and/or different target stimulation sites within patient 12 by electrically coupling the one or more leads to the electrical connection assembly 202 that best supports the desired path between IMD 200 and the target tissue site. For example, the clinician may couple the lead to the lead connection assembly 202 that provides the shortest path between IMD 200 and the target tissue site, or the less tortuous path (e.g., with fewer turns). In this way, IMD 200 may be adaptable to different types of therapy systems or different patient anatomies.

IMD 200 may be implanted into patient 12 without specific regard to the orientation within patient 12, while still allowing for implantable leads to be received by electrical connection assemblies 202 according to four distinct directions for each the first therapy module and second therapy module. In this manner, IMD 200 may be useful for more than one implantation configuration within a patient 12. For example, regardless of whether IMD 200 is implanted in the lower back or upper chest of patient 12, both a first and second lead may be received by at least one of a first electrical connector 204A-204D and at least one of a second electrical connect 206A-206D, respectively, to electrically couple first lead to first therapy module 46 in anyone of the four directions described.

In some examples, some of the electrical connectors 204A-204D and 206A-206D may not be mated with a lead. In such examples, a protective member may be inserted into or seal the one or more of the unmated electrical connectors 204A-204D and 206A-206D in order to isolate the electrical components of the respective connectors from the internal environment of patient 12, as well as protect components of IMD 200 from fluid or other particle ingress. In this manner, the internal components IMD 200 may be adequately protected within patient 12 despite the presence of one or more unmated electrical connectors.

The relative shape of the outer housing of IMD 200 is not limited to the substantially square shape shown in FIG. 10. In some examples, IMD 200 may be configured in other suitable shapes having any suitable number of sides on which electrical connection assemblies may be positioned, such as, e.g., in a substantially triangular shape defining three sides. In such an example, IMD 200 may include three electrical connection assemblies rather than the four electrical connection assemblies 202A-D shown in FIG. 10, with each of the three sides including an electrical connection assembly. As another, IMD 200 may be configured in a substantially circular shape. In such an example, IMD 200 may include one or more electrical connection assemblies at any location around the circumference of the IMD 200. Moreover, a housing of IMD 200 or any other IMD described herein may comprise any suitable outer surface, such as a nonplanar outer surface, which may be less irritating to tissue of patient 12.

The lead connection assemblies described herein are merely examples of the disclosure and the disclosure is not limited to such configurations. Instead, in some examples, any suitable electrical connectors known in the art may be utilized, e.g., to result in at therapy system having a first lead that is incompatible with a second electrical connector, as described herein. Furthermore, examples of the present disclosure may not be limited to therapy systems configured to deliver two different types of stimulation therapy to a patient. In some examples, an IMD may include two or more therapy modules configured to deliver different two or more types of stimulation therapies to a patient. In such cases, a lead connection assembly may include two or more electrical connectors that correspond to each therapy module.

In general, configuration of the electrical connectors of lead connection assemblies described herein may be modified to be consistent with the type of lead being used to deliver electrical stimulation therapy to a patient from IMD and still be within the scope of the disclosure. For example, a number of electrical contacts of an electrical connector may correspond to the number of electrical contacts of a lead that is electrically connected to the electrical connector.

The techniques described in this disclosure, including those attributed to IMD 14 and programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 45 of IMD 14, any one or more parts of the techniques described herein may be implemented by a processor of one of IMD 14, programmer 24 or another computing device, alone or in combination with IMD 14 or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described herein. These and other examples are within the scope of the following claims.

The invention claimed is:

1. An implantable medical system comprising:
a housing;
a first therapy module enclosed within the housing and configured to generate at least one of a pacing, cardioversion or defibrillation therapy that is delivered to a heart of a patient;
a second therapy module enclosed within the housing and configured to generate electrical stimulation that is delivered to a tissue site within the patient; and
a lead connection assembly comprising:
a first electrical connector electrically coupled to the first therapy module and configured to electrically connect to a first lead that delivers the at least one of the pacing, cardioversion, and defibrillation therapy to the heart of the patient; and
a second electrical connector electrically coupled to the second therapy module and configured to electrically connect to a second lead that delivers the electrical stimulation to the tissue site, wherein the second electrical connector is configured to be at least partially incompatible with the first lead, and wherein, when uncoupled from the first lead, the first electrical connector defines a magnetic polarity different from a magnetic polarity defined by the second electrical connector when uncoupled from the second lead.

2. The implantable medical system of claim 1, wherein the tissue site comprises at least one of a nonmyocardial tissue site, and nonvascular cardiac tissue site.

3. The implantable medical system of claim 1, wherein the tissue site comprises at least one of an extravascular tissue site, and a tissue site proximate a nerve.

4. The implantable medical system of claim 1, wherein the first and second electrical connectors comprise at least one of a different size, a different shape, and a different electrical contact arrangement.

5. The implantable medical system of claim 1, wherein the second electrical connector is configured to be at least one of physically incompatible, and at least partially electrically incompatible with the first lead.

6. The implantable medical system of claim 1, further comprising the first lead, wherein the first lead comprises a proximal portion including one or more first electrical contacts in a first configuration, and the second electrical connector comprises one or more second electrical contacts in a second configuration that is different than the first configuration.

7. The implantable medical system of claim 6, wherein the second electrical connector is configured such that when the proximal portion of the first lead is introduced into the second electrical connector, the one or more first electrical contacts of the first lead do not substantially align with the one or more second electrical contacts of the second electrical connector.

8. The implantable medical system of claim 1, further comprising the first lead, wherein the first lead comprises a proximal portion defining a first physical dimension, and the second electrical connector comprises an opening defining a second physical dimension that is different than the first physical dimension.

9. The implantable medical system of claim 8, wherein the first physical dimension comprises a lead diameter, and the second physical dimension comprises an opening diameter, wherein the opening diameter is less that the lead diameter.

10. The implantable medical system of claim 1, wherein the first electrical connector is configured to be incompatible with the second lead.

11. The implantable medical system of claim 1, wherein the first electrical connector defines a first opening configured to receive the first lead and the second electrical connector defines a second opening configured to receive the second lead, wherein the first and second openings face different directions.

12. The implantable medical system of claim 1, wherein the electrical stimulation comprises a frequency of approximately 1 Hertz to approximately 100 Hertz.

13. The implantable medical system of claim 1, wherein the first electrical connector is marked with a first visible identifier and the second electrical connector is marked with a second visible identifier that is different than the first visible identifier.

14. The implantable medical system of claim 13, wherein the first and second visible identifiers comprise at least one of an alphanumeric identifier, a geometric identifier, and a color.

15. The implantable medical system of claim 1, wherein the second electrical connector comprises a component that is configured to electrically connect to an electrical contact of the second lead, the implantable medical system further comprising a processor that determines whether the component is electrically connected to the electrical contact of the second lead prior to controlling the second therapy module to deliver electrical stimulation to the patient via the second lead.

16. The implantable medical system of claim 1, wherein the first electrical connector comprises a component that is configured to electrically connect to an electrical contact of the first lead, the implantable medical system further comprising a processor that determines whether the component is electrically connected to the electrical contact of the first lead prior to controlling the first therapy module to deliver the generating at least one of pacing, cardioversion, and defibrillation therapy to the patient via the first lead.

17. The implantable medical system of claim 1, wherein the magnetic polarity defined by the first electrical connector when uncoupled from the first lead is substantially opposite a magnetic polarity defined by the second lead when uncoupled from the second electrical connector.

18. An implantable medical system comprising:
a housing;
means for generating at least one of pacing, cardioversion, and defibrillation therapy that is delivered to a heart of a patient, wherein the means for generating the at least one of pacing, cardioversion or defibrillation therapy is enclosed within the housing;
means for generating electrical stimulation that is delivered to a tissue site within the patient, wherein the means for generating electrical stimulation is enclosed within the housing; and
means for receiving leads, the means for receiving leads comprising:
means for electrically coupling a first lead to the means for generating the at least one of pacing, cardioversion, and defibrillation therapy; and
means for electrically coupling a second lead to the means for generating the electrical stimulation, wherein the means for electrically coupling the second lead to the means for generating electrical stimulation is configured to be at least partially incompatible with the first lead, and wherein, when uncoupled from the first lead, the means for electrically coupling the first lead to the means for generating the at least one of pacing, cardioversion, and defibrillation therapy defines a magnetic polarity that is different from a magnetic polarity defined by the means for electrically coupling the second lead to the means for generating the electrical stimulation when uncoupled from the second lead.

19. The implantable medical system of claim 18, wherein the means for electrically coupling the first lead to the means for generating the at least one of pacing, cardioversion, and defibrillation therapy and the means for electrically coupling the second lead to the means for generating the electrical stimulation comprise at least one of a different size, different shape, and different electrical contact arrangement.

20. The implantable medical system of claim 18, wherein the means for electrically coupling the first lead to the means for generating the at least one of pacing, cardioversion, and defibrillation therapy defines a first opening configured to receive the first lead and the means for electrically coupling the second lead to the means for generating the electrical stimulation defines a second opening configured to receive the second lead, wherein the first and second openings face different directions.

21. The implantable medical system of claim 18, wherein the magnetic polarity defined by means for electrically coupling the first lead to the means for generating the at least one of pacing, cardioversion, and defibrillation therapy when uncoupled from the first lead is substantially opposite a magnetic polarity defined by the second lead when uncoupled from the means for electrically coupling a second lead to the means for generating the electrical stimulation.

22. A method comprising:
delivering at least one of pacing, cardioversion, and defibrillation therapy to a heart of a patient with at least one electrode of a first lead that is electrically coupled to a first therapy module of an implantable medical device, wherein the implantable medical device comprises a first electrical connector that electrically connects the first lead to the first therapy module; and
delivering electrical stimulation to a tissue site within the patient with at least one electrode of a second lead that is electrically coupled to a second therapy module of the implantable medical device, wherein the implantable medical device comprises a second electrical connector that electrically connects the second lead to the second therapy module, wherein the second electrical connector is configured to be at least partially incompatible with the first lead, and wherein, when uncoupled from the first lead, the first electrical connector defines a magnetic polarity different from a magnetic polarity defined by the second electrical connector when uncoupled from the second lead.

23. The method of claim 22, wherein the tissue site comprises at least one of a nonmyocardial tissue site, and a nonvascular cardiac tissue site.

24. The method of claim 22, wherein the first and second electrical connectors comprise at least one of a different size, a different shape, and a different electrical contact arrangement.

25. The method of claim 22, wherein the second electrical connector is configured to be at least one of physically incompatible, and at least partially electrically incompatible with the first lead.

26. The method of claim 22, wherein the first lead comprises a proximal portion including one or more first electrical contacts in a first configuration, and the second electrical connector comprises one or more second electrical contacts in a second configuration that is different than the first configuration.

27. The method of claim 22, wherein the first lead comprises a proximal portion defining a first physical dimension, and the second electrical connector comprises an opening defining a second physical dimension that is different than the first physical dimension.

28. The method of claim 22, wherein the first electrical connector is configured to be at least partially incompatible with the second lead.

29. The method of claim 22, wherein the first electrical connector defines a first opening configured to receive the first lead and the second electrical connector defines a second opening configured to receive the second lead, wherein the first and second openings face different directions.

30. The method of claim 22, wherein delivering electrical stimulation to the tissue site within the patient comprises delivering electrical stimulation comprising a frequency of approximately 1 Hertz to approximately 100 Hertz.

31. The method of claim 22, wherein the magnetic polarity defined by the first electrical connector when uncoupled from the first lead is substantially opposite a magnetic polarity defined by the second lead when uncoupled from the second electrical connector.

* * * * *